(12) United States Patent
Wu et al.

(10) Patent No.: US 8,940,871 B2
(45) Date of Patent: *Jan. 27, 2015

(54) ENGINEERED ANTI-PROSTATE STEM CELL ANTIGEN (PSCA) ANTIBODIES FOR CANCER TARGETING

(75) Inventors: Anna M. Wu, Sherman Oaks, CA (US); Robert E. Reiter, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1005 days.

This patent is subject to a terminal disclaimer.

(21) Appl. No.: 12/293,860

(22) PCT Filed: Mar. 20, 2007

(86) PCT No.: PCT/US2007/007020
§ 371 (c)(1),
(2), (4) Date: Sep. 22, 2008

(87) PCT Pub. No.: WO2007/109321
PCT Pub. Date: Sep. 27, 2007

(65) Prior Publication Data
US 2009/0311181 A1     Dec. 17, 2009

Related U.S. Application Data

(60) Provisional application No. 60/784,192, filed on Mar. 20, 2006.

(51) Int. Cl.
| | | |
|---|---|---|
| C12P 21/08 | (2006.01) | |
| G01N 33/574 | (2006.01) | |
| A61K 51/10 | (2006.01) | |
| C07K 16/30 | (2006.01) | |
| C07K 16/46 | (2006.01) | |
| A61K 39/00 | (2006.01) | |

(52) U.S. Cl.
CPC ...... G01N 33/57434 (2013.01); A61K 51/1072 (2013.01); A61K 51/1087 (2013.01); C07K 16/3069 (2013.01); C07K 16/464 (2013.01); A61K 2039/505 (2013.01); C07K 2317/526 (2013.01); C07K 2317/622 (2013.01); C07K 2317/64 (2013.01); C07K 2319/30 (2013.01)
USPC .................. 530/387.3; 530/350; 530/388.22; 530/388.8

(58) Field of Classification Search
USPC ............ 530/387.1, 387.3, 350, 388.22, 388.8
See application file for complete search history.

(56) References Cited

U.S. PATENT DOCUMENTS

| | | | |
|---|---|---|---|
| 4,444,878 A | 4/1984 | Paulus | |
| 4,892,824 A | 1/1990 | Skaletsky | |
| 4,943,525 A | 7/1990 | Dawson | |
| 5,256,395 A | 10/1993 | Barbet et al. | |
| 5,292,668 A | 3/1994 | Paulus | |
| 5,332,567 A | 7/1994 | Goldenberg | |
| 5,376,249 A | 12/1994 | Afeyan et al. | |
| 5,434,131 A | 7/1995 | Linsley | |
| 5,436,170 A | 7/1995 | Cornell | |
| 5,455,030 A | 10/1995 | Ladner et al. | |
| 5,491,088 A | 2/1996 | Hellstrom | |
| 5,518,889 A | 5/1996 | Ladner et al. | |
| 5,523,210 A | 6/1996 | Paulus | |
| 5,534,254 A | 7/1996 | Huston et al. | |
| 5,559,099 A | 9/1996 | Wickham | |
| 5,582,996 A | 12/1996 | Curtis | |
| 5,591,828 A | 1/1997 | Bosslet et al. | |
| 5,627,078 A | 5/1997 | Karl et al. | |
| 5,637,481 A | 6/1997 | Ledbetter et al. | |
| 5,660,827 A | 8/1997 | Thorpe | |
| 5,688,690 A | 11/1997 | Valiante et al. | |
| 5,693,477 A | 12/1997 | Cornell et al. | |
| 5,705,614 A | 1/1998 | Ring | |
| 5,712,136 A | 1/1998 | Wickham et al. | |
| 5,731,168 A | 3/1998 | Carter | |
| 5,731,190 A | 3/1998 | Wickham | |
| 5,739,281 A | 4/1998 | Thorgersen | |
| 5,741,712 A | 4/1998 | Cornell | |
| 5,747,035 A | 5/1998 | Presta et al. | |
| 5,747,037 A | 5/1998 | Noelle | |
| 5,762,930 A | 6/1998 | Fanger et al. | |
| 5,766,960 A | 6/1998 | Cornell | |
| 5,770,197 A | 6/1998 | Linsley | |
| 5,773,253 A | 6/1998 | Linsley | |
| 5,807,706 A | 9/1998 | Carter | |
| 5,821,333 A | 10/1998 | Carter et al. | |
| 5,830,473 A | 11/1998 | Thierfelder | |
| 5,830,478 A | 11/1998 | Raso et al. | |
| 5,837,242 A | 11/1998 | Holliger et al. | |

(Continued)

FOREIGN PATENT DOCUMENTS

| | | |
|---|---|---|
| EP | 1005494 | 10/1998 |
| EP | 1780268 A2 | 12/1999 |

(Continued)

OTHER PUBLICATIONS

Hu, S-Z. et al., "Minibody: A Novel Engineered Anti-Carcinoembryonic Antigen Antibody Fragment (Single-Chain Fv-$C_H3$) Which Exhibits Rapid, High-Level Targeting of Xenografts," Cancer Research, Jul. 1, 1996, vol. 56, pp. 3055-3061.

(Continued)

Primary Examiner — Stephen Rawlings
(74) Attorney, Agent, or Firm — Morgan, Lewis & Bockius LLP; Annette S. Parent

(57) ABSTRACT

The invention provides novel humanized antibody fragments that specifically bind prostate cell-surface antigen (PSCA), a protein which is overexpressed in variety of cancers, including prostate, bladder, and pancreatic cancer. Methods are provided for the use of the compositions of the invention for the treatment of cancer, diagnosis of cancer, to provide a prognosis of cancer progression, and for cancer imaging.

10 Claims, 21 Drawing Sheets

(56) References Cited

U.S. PATENT DOCUMENTS

| | | |
|---|---|---|
| 5,837,281 A | 11/1998 | Iga et al. |
| 5,837,821 A | 11/1998 | Wu |
| 5,840,854 A | 11/1998 | Hellstrom et al. |
| 5,844,094 A | 12/1998 | Hudson et al. |
| 5,844,095 A | 12/1998 | Linsley |
| 5,846,782 A | 12/1998 | Wickham |
| 5,851,527 A | 12/1998 | Hansen |
| 5,851,795 A | 12/1998 | Linsley |
| 5,852,186 A | 12/1998 | Sodroski et al. |
| 5,855,866 A | 1/1999 | Thorpe |
| 5,861,156 A | 1/1999 | George et al. |
| 5,863,538 A | 1/1999 | Thorpe |
| 5,863,765 A | 1/1999 | Berry et al. |
| 5,869,045 A | 2/1999 | Hellstrom |
| 5,869,049 A | 2/1999 | Noelle et al. |
| 5,869,620 A | 2/1999 | Whitlow et al. |
| 5,872,222 A | 2/1999 | Chang |
| 5,876,691 A | 3/1999 | Chester et al. |
| 5,876,718 A | 3/1999 | Noelle |
| 5,877,289 A | 3/1999 | Thorpe |
| 5,877,291 A | 3/1999 | Mezes et al. |
| 5,885,579 A | 3/1999 | Linsley |
| 5,885,796 A | 3/1999 | Linsley |
| 5,892,020 A | 4/1999 | Mezes |
| 5,917,018 A | 6/1999 | Thorgersen |
| 5,932,448 A | 8/1999 | Tso et al. |
| 5,942,229 A | 8/1999 | Noelle et al. |
| 5,951,982 A | 9/1999 | Zoller et al. |
| 5,959,083 A | 9/1999 | Bosslet et al. |
| 5,962,311 A | 10/1999 | Wickham |
| 5,965,132 A | 10/1999 | Thorpe |
| 5,965,541 A | 10/1999 | Wickham |
| 5,968,510 A | 10/1999 | Linsley |
| 5,977,318 A | 11/1999 | Linsley |
| 5,980,896 A | 11/1999 | Hellstrom et al. |
| 5,989,830 A | 11/1999 | Davis et al. |
| 5,990,275 A | 11/1999 | Whitlow et al. |
| 5,994,519 A | 11/1999 | Osbourn |
| 6,004,554 A | 12/1999 | Thorpe |
| 6,004,555 A | 12/1999 | Thorpe |
| 6,010,884 A | 1/2000 | Griffiths |
| 6,010,902 A | 1/2000 | Ledbetter et al. |
| 6,020,145 A | 2/2000 | Hellstrom |
| 6,030,792 A | 2/2000 | Otterness et al. |
| 6,051,230 A | 4/2000 | Thorpe |
| 6,057,155 A | 5/2000 | Wickham |
| 6,071,490 A | 6/2000 | Bates et al. |
| 6,083,477 A | 7/2000 | Goldenberg |
| 6,083,763 A | 7/2000 | Balch |
| 6,090,914 A | 7/2000 | Linsley |
| 6,093,399 A | 7/2000 | Thorpe |
| 6,096,289 A | 8/2000 | Goldenberg |
| 6,096,871 A | 8/2000 | Presta et al. |
| 6,099,841 A | 8/2000 | Hillan et al. |
| 6,106,835 A | 8/2000 | Chang |
| 6,117,982 A | 9/2000 | Chang |
| 6,121,022 A | 9/2000 | Presta et al. |
| 6,129,916 A | 10/2000 | Chang |
| 6,132,992 A | 10/2000 | Ledbetter |
| 6,150,508 A | 11/2000 | Murphy et al. |
| 6,180,336 B1 | 1/2001 | Osbourn |
| 6,187,284 B1 | 2/2001 | Griffiths |
| 6,193,966 B1 | 2/2001 | Deo et al. |
| 6,193,967 B1 | 2/2001 | Morganelli |
| 6,197,298 B1 | 3/2001 | Chang |
| 6,200,765 B1 | 3/2001 | Murphy et al. |
| 6,201,167 B1 | 3/2001 | Pothier |
| 6,241,961 B1 | 6/2001 | Benes et al. |
| 6,248,516 B1 | 6/2001 | Winter et al. |
| 6,258,939 B1 | 7/2001 | Reiter et al. |
| 6,261,535 B1 | 7/2001 | Thorpe |
| 6,261,789 B1 | 7/2001 | Reiter |
| 6,261,791 B1 | 7/2001 | Reiter |
| 6,267,960 B1 | 7/2001 | Reiter et al. |
| 6,284,742 B1 | 9/2001 | Curiel et al. |
| 6,290,955 B1 | 9/2001 | Thierfelder |
| 6,294,391 B1 | 9/2001 | Badley et al. |
| 6,312,692 B1 | 11/2001 | Noelle |
| 6,312,694 B1 | 11/2001 | Thorpe et al. |
| 6,312,960 B1 | 11/2001 | Balch |
| 6,319,500 B1 | 11/2001 | Goldenberg |
| 6,329,190 B1 | 12/2001 | Wickham |
| 6,331,441 B1 | 12/2001 | Balch |
| 6,342,219 B1 | 1/2002 | Thorpe |
| 6,342,221 B1 | 1/2002 | Thorpe |
| 6,342,587 B1 | 1/2002 | Barbas, III et al. |
| 6,342,588 B1 | 1/2002 | Osbourn |
| 6,346,249 B1 | 2/2002 | Barbas, III |
| 6,358,489 B1 | 3/2002 | Griffiths |
| 6,361,774 B1 | 3/2002 | Griffiths et al. |
| 6,368,596 B1 | 4/2002 | Ghetie et al. |
| 6,383,759 B1 | 5/2002 | Murphy et al. |
| 6,387,350 B2 | 5/2002 | Goldenberg |
| 6,395,276 B1 | 5/2002 | Rybak |
| 6,399,068 B1 | 6/2002 | Goldenberg |
| 6,416,758 B1 | 7/2002 | Thorpe |
| 6,451,312 B1 | 9/2002 | Thorpe |
| 6,458,933 B1 | 10/2002 | Hansen |
| 6,465,253 B1 | 10/2002 | Wickham |
| 6,479,301 B1 | 11/2002 | Balch |
| 6,482,919 B2 | 11/2002 | Ledbetter |
| 6,489,123 B2 | 12/2002 | Osbourn |
| 6,492,123 B1 | 12/2002 | Holliger |
| 6,524,583 B1 | 2/2003 | Thorpe |
| 6,541,212 B2 | 4/2003 | Reiter et al. |
| 6,545,142 B1 | 4/2003 | Winter |
| 6,548,275 B2 | 4/2003 | Goldenberg |
| 6,573,096 B1 | 6/2003 | Chen |
| 6,589,527 B1 | 7/2003 | Winter |
| 6,602,684 B1 | 8/2003 | Umana et al. |
| 6,623,940 B1 | 9/2003 | Ledbetter |
| 6,642,007 B1 | 11/2003 | Saltarelli |
| 6,649,163 B1 | 11/2003 | Bander |
| 6,649,407 B2 | 11/2003 | Wickham |
| 6,653,104 B2 | 11/2003 | Goldenberg |
| 6,676,941 B2 | 1/2004 | Thorpe |
| 6,703,020 B1 | 3/2004 | Thorpe |
| 6,709,844 B1 | 3/2004 | Levy |
| 6,749,853 B1 | 6/2004 | Thorpe |
| 6,756,036 B2 | 6/2004 | Reiter |
| 6,790,939 B2 | 9/2004 | Reiter |
| 6,803,238 B1 | 10/2004 | Eggers |
| 6,824,780 B1 | 11/2004 | Devaux et al. |
| 6,825,326 B2 | 11/2004 | Reiter |
| 6,835,866 B1 | 12/2004 | Mangelsdorf et al. |
| 6,861,234 B1 | 3/2005 | Simard et al. |
| 6,869,620 B2 | 3/2005 | Moore |
| 6,870,034 B2 | 3/2005 | Breece et al. |
| 6,881,822 B2 | 4/2005 | Reiter |
| 6,887,468 B1 | 5/2005 | Thorpe |
| 6,887,471 B1 | 5/2005 | Linsley |
| 6,887,975 B2 | 5/2005 | Afar et al. |
| 6,951,755 B2 | 10/2005 | Wickham |
| 6,953,567 B2 | 10/2005 | Griffiths |
| 6,960,443 B2 | 11/2005 | Reiter |
| 6,962,981 B1 | 11/2005 | Murphy |
| 6,977,074 B2 | 12/2005 | Kundig et al. |
| 6,979,730 B2 | 12/2005 | Reiter |
| 6,994,851 B1 | 2/2006 | Kundig et al. |
| 6,998,253 B1 | 2/2006 | Presta |
| 7,033,572 B2 | 4/2006 | Goldenberg |
| 7,033,798 B2 | 4/2006 | Plückthun et al. |
| 7,053,186 B2 | 5/2006 | Afar et al. |
| 7,056,509 B2 | 6/2006 | Thorpe |
| 7,105,166 B1 | 9/2006 | Linsley |
| 7,112,317 B2 | 9/2006 | Thorpe |
| 7,122,646 B2 | 10/2006 | Holliger |
| 7,125,541 B2 | 10/2006 | Thorpe |
| 7,159,826 B1 | 1/2007 | Aberdeen |
| 7,201,890 B2 | 4/2007 | Goldenberg |
| 7,201,900 B2 | 4/2007 | Murphy |
| 7,230,084 B2 | 6/2007 | Hansen |
| 7,232,682 B2 | 6/2007 | Simard et al. |
| 7,235,641 B2 | 6/2007 | Kufer et al. |

(56) References Cited

U.S. PATENT DOCUMENTS

| | | |
|---|---|---|
| 7,250,492 B2 | 7/2007 | Chen |
| 7,306,907 B2 | 12/2007 | Winter |
| 7,311,910 B2 | 12/2007 | Linsley |
| 7,323,553 B2 | 1/2008 | Fahrner et al. |
| 7,364,729 B2 | 4/2008 | Kundig et al. |
| 7,375,078 B2 | 5/2008 | Feng |
| 7,381,407 B1 | 6/2008 | Murphy |
| 7,390,654 B2 | 6/2008 | Levy |
| 7,407,656 B2 | 8/2008 | Reiter |
| 7,413,852 B2 | 8/2008 | Balch |
| 7,417,113 B2 | 8/2008 | Reiter |
| 7,435,416 B2 | 10/2008 | Devaux et al. |
| 7,452,539 B2 | 11/2008 | Emery et al. |
| 7,462,691 B2 | 12/2008 | Reiter |
| 7,470,429 B2 | 12/2008 | Griffiths |
| 7,476,385 B2 | 1/2009 | Noelle |
| 7,476,513 B2 | 1/2009 | Murphy |
| 7,485,296 B2 | 2/2009 | Reiter |
| 7,485,704 B2 | 2/2009 | Fahrner et al. |
| 7,494,646 B2 | 2/2009 | Jakobovits et al. |
| 7,498,298 B2 | 3/2009 | Doronina et al. |
| 7,517,670 B2 | 4/2009 | Umana et al. |
| 7,521,541 B2 | 4/2009 | Eigenbrot et al. |
| 7,524,813 B2 | 4/2009 | Zundel et al. |
| 7,527,786 B2 | 5/2009 | Reiter |
| 7,541,442 B2 | 6/2009 | Gudas et al. |
| 7,572,772 B2 | 8/2009 | Linsley |
| 7,595,379 B2 | 9/2009 | Gudas et al. |
| 7,612,181 B2 | 11/2009 | Wu et al. |
| 7,622,564 B2 | 11/2009 | Ge et al. |
| 7,622,569 B2 | 11/2009 | Raitano et al. |
| 7,642,228 B2 | 1/2010 | Carter |
| 7,662,936 B2 | 2/2010 | Kadkhodayan et al. |
| 7,691,380 B2 | 4/2010 | Thorpe |
| 7,695,936 B2 | 4/2010 | Carter |
| 7,722,874 B2 | 5/2010 | Noelle |
| 7,745,394 B2 | 6/2010 | Doronina et al. |
| 7,754,681 B2 | 7/2010 | Feng |
| 7,807,799 B2 | 10/2010 | Fahrner et al. |
| 7,820,166 B2 | 10/2010 | Lanzavecchia |
| 7,838,637 B2 | 11/2010 | Kontermann |
| 7,855,275 B2 | 12/2010 | Eigenbrot et al. |
| 7,867,483 B2 | 1/2011 | Delcayre et al. |
| 7,884,179 B2 | 2/2011 | Faris et al. |
| 7,888,035 B2 | 2/2011 | Klass et al. |
| 7,897,356 B2 | 3/2011 | Klass et al. |
| 7,906,329 B2 | 3/2011 | Umana et al. |
| 7,915,395 B2 | 3/2011 | Ledbetter |
| 7,939,503 B2 | 5/2011 | Jakobovits et al. |
| 7,947,276 B2 | 5/2011 | Jakobovits et al. |
| 7,947,839 B2 | 5/2011 | Gazzard et al. |
| 7,960,109 B2 | 6/2011 | Hessels et al. |
| 7,964,566 B2 | 6/2011 | Doronina et al. |
| 7,964,567 B2 | 6/2011 | Doronina et al. |
| 7,989,434 B2 | 8/2011 | Feng |
| 7,994,135 B2 | 8/2011 | Doronina et al. |
| 7,998,701 B2 | 8/2011 | Chua et al. |
| 8,007,994 B2 | 8/2011 | Mangelsdorf et al. |
| 8,008,442 B2 | 8/2011 | Jakobovits et al. |
| 8,012,937 B2 | 9/2011 | Raitano et al. |
| 8,013,128 B2 | 9/2011 | Gudas et al. |
| 8,013,135 B2 | 9/2011 | Jakobovits et al. |
| 8,088,908 B2 | 1/2012 | Sherman et al. |
| 8,206,932 B2 | 6/2012 | Gudas et al. |
| 8,278,424 B2 | 10/2012 | Gudas et al. |
| 8,309,300 B2 | 11/2012 | Junutula et al. |
| 2001/0006618 A1 | 7/2001 | Goldenberg |
| 2001/0055595 A1 | 12/2001 | Goldenberg |
| 2001/0055751 A1 | 12/2001 | Saffran |
| 2002/0004215 A1 | 1/2002 | Osbourn et al. |
| 2002/0012989 A1 | 1/2002 | Ledbetter |
| 2002/0037289 A1 | 3/2002 | Thorpe et al. |
| 2002/0102666 A1 | 8/2002 | Reiter |
| 2002/0114808 A1 | 8/2002 | Griffiths |
| 2002/0119096 A1 | 8/2002 | Griffiths |
| 2002/0119153 A1 | 8/2002 | Thorpe et al. |
| 2002/0119157 A1 | 8/2002 | Reiter |
| 2002/0132979 A1 | 9/2002 | Chen |
| 2002/0136689 A1 | 9/2002 | Reiter et al. |
| 2002/0136690 A1 | 9/2002 | Goldenberg |
| 2002/0141941 A1 | 10/2002 | Reiter |
| 2002/0146369 A1 | 10/2002 | Goldenberg |
| 2002/0151027 A1 | 10/2002 | Wickham |
| 2002/0155537 A1 | 10/2002 | Carter |
| 2002/0187135 A1 | 12/2002 | Noelle |
| 2002/0187153 A1 | 12/2002 | Goldenberg |
| 2002/0192223 A1 | 12/2002 | Hellstrom |
| 2003/0022355 A1 | 1/2003 | Wickham |
| 2003/0031669 A1 | 2/2003 | Goldenberg |
| 2003/0068322 A1 | 4/2003 | Hansen |
| 2003/0103982 A1 | 6/2003 | Hansen |
| 2003/0113818 A1 | 6/2003 | Reiter |
| 2003/0113820 A1 | 6/2003 | Reiter |
| 2003/0114368 A1 | 6/2003 | Rybak |
| 2003/0114659 A1 | 6/2003 | Winter |
| 2003/0118583 A1 | 6/2003 | Emery et al. |
| 2003/0130496 A1 | 7/2003 | Winter |
| 2003/0147806 A1 | 8/2003 | Reiter |
| 2003/0153016 A1 | 8/2003 | Reiter |
| 2003/0170228 A1 | 9/2003 | Ashkenazi et al. |
| 2003/0170697 A1 | 9/2003 | Goldenberg |
| 2003/0175900 A1 | 9/2003 | Ashkenazi et al. |
| 2003/0185832 A1 | 10/2003 | Thorpe |
| 2003/0211096 A1 | 11/2003 | Ashkenazi et al. |
| 2003/0219441 A1 | 11/2003 | Thorpe |
| 2003/0219876 A1 | 11/2003 | Ledbetter |
| 2003/0228318 A1 | 12/2003 | Reiter |
| 2004/0018519 A1 | 1/2004 | Wright, Jr. |
| 2004/0018571 A1 | 1/2004 | Reiter |
| 2004/0023249 A1 | 2/2004 | Balch |
| 2004/0024188 A1 | 2/2004 | Murphy |
| 2004/0038339 A1 | 2/2004 | Kufer et al. |
| 2004/0043029 A1 | 3/2004 | Hellstrom |
| 2004/0058400 A1 | 3/2004 | Holliger |
| 2004/0110941 A2 | 6/2004 | Winter |
| 2004/0115202 A1 | 6/2004 | Chen |
| 2004/0162411 A1 | 8/2004 | Lanzavecchia |
| 2004/0241817 A1 | 12/2004 | Umana et al. |
| 2005/0003465 A1 | 1/2005 | Reiter |
| 2005/0026178 A1 | 2/2005 | Nilsen-Hamilton |
| 2005/0026229 A1 | 2/2005 | Reiter |
| 2005/0036942 A1 | 2/2005 | Devaux et al. |
| 2005/0059099 A1 | 3/2005 | Reiter |
| 2005/0069543 A1 | 3/2005 | Thierfelder |
| 2005/0136050 A1 | 6/2005 | Kufer et al. |
| 2005/0152909 A1 | 7/2005 | Reiter |
| 2005/0163780 A1 | 7/2005 | Noelle |
| 2005/0169919 A1 | 8/2005 | Linsley |
| 2005/0169930 A1 | 8/2005 | Reiter |
| 2005/0175582 A1 | 8/2005 | Goldenberg |
| 2005/0215769 A1 | 9/2005 | Breece et al. |
| 2005/0232929 A1 | 10/2005 | Kadkhodayan et al. |
| 2005/0239116 A1 | 10/2005 | Willey |
| 2005/0249738 A1 | 11/2005 | Goldenberg |
| 2005/0272128 A1 | 12/2005 | Umana et al. |
| 2005/0277193 A1 | 12/2005 | Wickham |
| 2006/0018914 A1 | 1/2006 | Hellstrom |
| 2006/0147375 A1 | 7/2006 | Gudas et al. |
| 2006/0159689 A1 | 7/2006 | Chiang et al. |
| 2006/0210473 A1 | 9/2006 | Thorpe |
| 2006/0222649 A1 | 10/2006 | Noelle |
| 2006/0234226 A1 | 10/2006 | Fahner et al. |
| 2006/0234271 A1 | 10/2006 | Su |
| 2006/0246524 A1 | 11/2006 | Bauer et al. |
| 2006/0269540 A1 | 11/2006 | Robert et al. |
| 2006/0269557 A1 | 11/2006 | Sherman et al. |
| 2006/0275312 A1 | 12/2006 | Chua et al. |
| 2007/0014794 A1 | 1/2007 | Carter |
| 2007/0031922 A1 | 2/2007 | Presta |
| 2007/0059306 A1 | 3/2007 | Grosmaire |
| 2007/0128671 A1 | 6/2007 | Murphy |
| 2007/0134243 A1 | 6/2007 | Gazzard et al. |
| 2007/0207146 A1 | 9/2007 | Hansen |
| 2007/0212331 A1 | 9/2007 | Baldassare et al. |

(56) References Cited

U.S. PATENT DOCUMENTS

| | | |
|---|---|---|
| 2007/0243950 A1 | 10/2007 | Billings |
| 2007/0253950 A1 | 11/2007 | Jacobsen |
| 2007/0286858 A1 | 12/2007 | Clancy |
| 2008/0031876 A1 | 2/2008 | Linsley |
| 2008/0166759 A1 | 7/2008 | Presta |
| 2008/0171040 A1 | 7/2008 | Ebens et al. |
| 2008/0206192 A1 | 8/2008 | Moller et al. |
| 2008/0213256 A1 | 9/2008 | Kufer et al. |
| 2008/0213921 A1 | 9/2008 | Robertson et al. |
| 2008/0227736 A1 | 9/2008 | Chen et al. |
| 2008/0267872 A1 | 10/2008 | Raitano et al. |
| 2008/0299618 A1 | 12/2008 | Winter |
| 2008/0305105 A1 | 12/2008 | Kufer et al. |
| 2008/0305476 A1 | 12/2008 | Robertson et al. |
| 2008/0318253 A9 | 12/2008 | Reiter |
| 2008/0318254 A9 | 12/2008 | Reiter |
| 2009/0004109 A1 | 1/2009 | Jacobovits et al. |
| 2009/0022738 A1 | 1/2009 | Hofmeister et al. |
| 2009/0041758 A1 | 2/2009 | Glaser |
| 2009/0041791 A1 | 2/2009 | Feng |
| 2009/0053223 A1 | 2/2009 | Hoffmann et al. |
| 2009/0099344 A1 | 4/2009 | Fahrner et al. |
| 2009/0104631 A1 | 4/2009 | Reiter |
| 2009/0136475 A1 | 5/2009 | Barth |
| 2009/0169613 A1 | 7/2009 | Reznik et al. |
| 2009/0202548 A1 | 8/2009 | Gudas et al. |
| 2009/0214539 A1 | 8/2009 | Grosmaire |
| 2009/0226465 A1 | 9/2009 | Jackson |
| 2009/0238755 A1 | 9/2009 | Bander |
| 2009/0239759 A1 | 9/2009 | Balch |
| 2009/0272169 A1 | 11/2009 | Pan |
| 2009/0275081 A1 | 11/2009 | Barat et al. |
| 2009/0286258 A1 | 11/2009 | Kaur et al. |
| 2009/0311181 A1 | 12/2009 | Wu |
| 2009/0317397 A1 | 12/2009 | Linsley |
| 2010/0003766 A1 | 1/2010 | Eigenbrot et al. |
| 2010/0034837 A1 | 2/2010 | Beria et al. |
| 2010/0047239 A1 | 2/2010 | Wu et al. |
| 2010/0055120 A1 | 3/2010 | Ge et al. |
| 2010/0058803 A1 | 3/2010 | Ransbarger |
| 2010/0069616 A1 | 3/2010 | Wu et al. |
| 2010/0111856 A1 | 5/2010 | Gill et al. |
| 2010/0135900 A1 | 6/2010 | Cerveny |
| 2010/0184046 A1 | 7/2010 | Klass et al. |
| 2010/0189651 A1 | 7/2010 | Stagliano |
| 2010/0215581 A1 | 8/2010 | Hoffmann |
| 2010/0254986 A1 | 10/2010 | Carter |
| 2010/0255479 A1 | 10/2010 | Mikolajczyk et al. |
| 2010/0266491 A1 | 10/2010 | Farokhzad et al. |
| 2010/0267933 A1 | 10/2010 | Wilson |
| 2010/0278919 A1 | 11/2010 | Denes et al. |
| 2010/0297004 A1 | 11/2010 | Wu et al. |
| 2010/0303821 A1 | 12/2010 | Ashman |
| 2011/0006466 A1 | 1/2011 | Ichikawa |
| 2011/0009001 A1 | 1/2011 | Chen |
| 2011/0020327 A1 | 1/2011 | Moya et al. |
| 2011/0076287 A1 | 3/2011 | Cohen et al. |
| 2011/0081345 A1 | 4/2011 | Moore |
| 2011/0086050 A1 | 4/2011 | Presta |
| 2011/0104059 A1 | 5/2011 | St. Croix et al. |
| 2011/0110852 A1 | 5/2011 | Miller et al. |
| 2011/0117023 A1 | 5/2011 | Yamauchi |
| 2011/0123532 A1 | 5/2011 | Gurney et al. |
| 2011/0137017 A1 | 6/2011 | Eigenbrot et al. |
| 2011/0142811 A1 | 6/2011 | Ungerechts |
| 2011/0207155 A1 | 8/2011 | Pengo et al. |
| 2011/0262968 A1 | 10/2011 | Gudas et al. |
| 2011/0268656 A1 | 11/2011 | Ho |

FOREIGN PATENT DOCUMENTS

| | | |
|---|---|---|
| EP | 1550729 | 7/2005 |
| EP | 1997514 | 12/2008 |
| EP | 1629011 B1 | 1/2010 |
| EP | 2226394 A1 | 9/2010 |
| EP | 2260858 A2 | 12/2010 |
| JP | 2003-504414 | 2/2003 |
| WO | WO 93/15199 | 8/1993 |
| WO | WO 94/09820 | 5/1994 |
| WO | WO 96/08570 | 3/1996 |
| WO | WO 96/26272 | 8/1996 |
| WO | WO 97/35616 | 10/1997 |
| WO | WO 99/56779 | 11/1999 |
| WO | WO 00/14234 | 3/2000 |
| WO | WO 01/05427 | 1/2001 |
| WO | WO 01/05427 A1 | 1/2001 |
| WO | WO 01/09303 | 2/2001 |
| WO | WO 01/40309 A2 | 6/2001 |
| WO | WO 01/40309 A3 | 6/2001 |
| WO | WO 01/82963 | 11/2001 |
| WO | WO 02/22680 | 3/2002 |
| WO | WO 03/008537 | 1/2003 |
| WO | WO 03/050140 | 6/2003 |
| WO | WO 2004/106380 | 12/2004 |
| WO | WO 2005/000899 | 1/2005 |
| WO | WO 2005/026334 | 3/2005 |
| WO | WO 2005/043165 | 5/2005 |
| WO | WO 2005/061547 | 7/2005 |
| WO | WO 2005/068616 | 7/2005 |
| WO | WO 2006/112933 | 10/2006 |
| WO | WO 2007/001476 | 1/2007 |
| WO | WO 2007/064345 | 6/2007 |
| WO | WO 2007/100385 | 9/2007 |
| WO | WO 2007/109321 | 9/2007 |
| WO | WO 2007/137117 | 11/2007 |
| WO | WO 2009/003492 | 1/2009 |
| WO | WO 2009/032949 | 3/2009 |
| WO | WO 2009/039854 | 4/2009 |
| WO | WO 2009/052328 | 4/2009 |
| WO | WO 2009/076099 | 6/2009 |
| WO | WO 2009/082443 | 7/2009 |
| WO | WO 2010/037395 | 4/2010 |
| WO | WO 2010/037397 | 4/2010 |
| WO | WO 2010/037539 | 4/2010 |
| WO | WO 2010/037835 | 4/2010 |
| WO | WO 2010/102195 | 9/2010 |
| WO | WO 2011/000054 | 1/2011 |
| WO | WO 2011/056983 | 5/2011 |
| WO | WO 2011/069019 | 6/2011 |
| WO | WO 2011/075786 | 6/2011 |
| WO | WO 2011/090762 | 7/2011 |
| WO | WO 2011/109440 | 9/2011 |

OTHER PUBLICATIONS

Wu, A.M. et al., "High-Resolution MicroPET Imaging of Carcinoembryonic Antigen-Positive Xenografts by Using a Copper-64-Labeled Engineered Antibody Fragment," *PNAS*, Jul. 18, 2000, vol. 97, No. 15, pp. 8495-8500.

Extracts from Janeway and Travers, Immuno. Biology, 3rd Ed. 1997.

Gu et al., Oncogene, 19: 1288-1296 (2000) Prostrate stem cell antigen (PSCA) expression increases with high gleason score, advanced stage and bone metastasis in prostate cancer.

Hopp and Woods, Mol. Immunol. 20: pp. 483-489 (1983) A computer program for predicting protein antigenic determinants.

Horoszewicz J.S. et. al., Anticancer Res. 7: pp. 927-936, (1987) Monoclonal antibodies to a new antigenic marker in epithelial prostatic cells and serum of prostatic cancer patients.

Olafsen, T. et al., J. Immunother, 30:4 396 (2007) Targeting, Imaging, and Therapy Using a Humanized Antiprostate Stem Cell antigen (PSCA) Antibody.

Persiani S et., al., Cancer Immunol Immunother (1989), 29: pp. 167-170 in vivo antitumor effect of methotrexate conjugated to a monoclonal IgM antibody specific for stage-specific embryonic antigen-1, on MH-15 mouse teratocarcinoma.

Tazzari P.L. et al., Cancer Immunol Immunother (1988) 26: pp. 231-236 an immunotoxin containing a rat IgM monoclonal antibody (Campath 1) and saporin 6: effect on T lymphocytes and hemopoietic cells.

Usui H. et. al., Acta Med Okayama, 1994; 48 (6): pp. 305-309 Evaluation of Ricin a Chain-Containing Immunotoxins Directed Against Glycolipid and Glycoprotein on Mouse Lymphoma Cells.

(56) References Cited

OTHER PUBLICATIONS

Wiedloha A. et. al., Archivum Immunologiae et Therapiae Experimentalis, 1989, 37, pp. 101-113 Specific killing of mouse leukemic cells with ricin A-chain immunotoxin.

Wiels J. et. at., Cancer Research 44, pp. 129-133, Jan. 1984 Properties of immunotoxins against a glycolipid antigen associated with Burkitt's lymphoma.

Wu, A.M. et al. "Arming antibodies: prospects and challenges for immunoconjugates." Nature Biotechnology, Sep. 2007, vol. 23: pp. 1137-1146.

Notice of Opposition to European Patent Application no. 0668777 filed Jul. 11, 2007 by BZL Biologics LLC.

Notice of Opposition to European Patent Application No. 0956506 filed Dec. 1, 2006 by PSMA Development Company LLC.

Olafsen, T. Cancer Biotherapy & Radiopharmaceuticals, "Micropet Evaluation of an I-124-Labeled Antibody Fragment (SCFV-FC) in Non-Internalizing (CDP and CD20) Versus Internalizing (HER2 and PSCA) Tumor Antigen Systems" vol. 21, No. 4 (2006).

U.S. Appl. No. 13/554,306, filed Jul. 20, 2012, Wu et al.

Adams et al., "Highly specific in vivo tumor targeting by monovalent and divalent forms of 741F8 anti-c-erbB-2 single-chain Fv." Cancer Res. 53.17 (Sep. 1, 1993): 4026-34.

Albrecht et al., "Development of anti-MUC1 di-scFvs for molecular targeting of epithelial cancers, such as breast and prostate cancers." Q J Nucl Med Mol Imaging 51.4 (Dec. 2007): 304-13.

Atwell et al., "scFv multimers of the anti-neuranminidase antibody NC10: length of the linker between $V_H$ and $V_L$ domains dictates precisely the transition between diabodies and triabodies," Protein Engineering, Jul. 1999, vol. 12, No. 7, pp. 597-604.

Barat et al., "Cys-diabody quantum dot conjugates (immunoQdots) for cancer marker detection." Bioconjug Chem. 20.8 (Aug. 19, 2009): 1474-81.

Carmichael et al., "The Crystal Structure of an Anti-CEA scFv Diabody Assembled from T84.66 scFvs in V(L)-to-V(H) Orientation: Implications for Diabody Flexibility." J. Mol. Biol. 326.2 (Feb. 14, 2003): 341-51.

Communication pursuant to Rules 70(2) and 70a(2) EPC dated Dec. 28, 2010, received in EP Appl. No. 08799192.3, 11 pages.

Desplancq et al., "Multimerization behaviour of single chain Fv variants for the tumour-binding antibody B72.3," Protein Engineering, Aug. 1994, vol. 7, No. 8, pp. 1027-1033.

Fitzgerald et al., "Improved Tumor Targeting by Disulphide Stabilized Diabodies Expressed in Pichia Pastoris." Protein Engineering 10.10 (1997): 1221-1225.

Glockshuber et al., "A Comparison of Strategies to Stabilize Immunoglobulin $F_v$-Fragments." Biochemistry 29.6 (1990): 1362-1367.

Hollinger et al., "Diabodies: Small Bivalent and Bispecific Antibody Fragments." Proc. Natl. Acad. Sci. USA 90 (Jul. 1993): 6444-6448.

Hu et al., "Minibody: A Novel Engineered Anti-carcinoembryonic Antigen Antibody Fragment (Single-Chain $F_v$–$C_H^3$) Which Exhibits Rapid, High-Level Targeting of Xenografts." Cancer Research 56 (Jul. 1, 1996): 3055-3061.

Written Opinion dated Apr. 23, 2008, from Int'l Appl. No. PCT/US2008/007020 (WO 2007/109321).

Written Opinion dated Apr. 22, 2008, from Int'l Appl. No. PCT/US2008/075291 (WO 2009/032949).

Johnson et al., "Effector cell recruitment with novel Fv-based dual-affinity re-targeting protein leads to potent tumor cytolysis and in vivo B-cell depletion." J Mol Biol. 399.3 (Jun. 11, 2010): 436-49.

Kim et al., "Anti-CD30 diabody-drug conjugates with potent antitumor activity." Mol Cancer Ther. 7.8 (Aug. 2008): 2486-97.

Leung et al., "Engineering a Unique Glycosylation Site for Site-Specific Conjugation of Haptens to Antibody Fragments." The Journal of Immunology 154 (1995): 5919-5926.

Li et al., "Improved biodistribution and radioimmunoimaging with poly(ethylene glycol)-DOTA-conjugated anti-CEA diabody." Bioconjug Chem. 17.1 (Jan-Feb 2006): 68-76.

Li et al., "Reduction of Kidney Uptake in Radiometal Labeled Peptide Linkers Conjugated to Recombinant Antibody Fragments, Site-Specific Conjugation of DOTA-Peptides to a Cys-Diabody." Bioconiugate Chem. 13.5 (2002): 985-995.

McCartney et al., "Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded throug C-termainal cysteinyl peptides." Protein Eng. 8.3 (Mar. 1995):301-14.

McCartney et al., Refolding of single-chain Fv with C-terminal cysteine (sFv); formation of disulfide-bonded homodimers of antic-Å£'r/7B-2 and anti-digoxin sFv', Miami Short Rep., 1993, vol. 3, p. 91.

Moore et al., "Application of dual affinity retargeting molecules to achieve optimal redirected T-cell killing of B-cell lymphoma." Blood 117.17 (Apr. 28, 2011): 4542-51.

Olafsen et al., "Covalent Disulfide-linked Anti-CEA Diabody Allows Site-specific Conjugation and Radiolabeling for Tumor Targeting Applications." Protein Engineering, Design & Selection 17.1 (2004): 21-27.

Olafsen et al., "ImmunoPET imaging of B-cell lymphoma using 1241-anti-CD20 scFv dimers (diabodies)." Protein Eng Des Sel. 23.4 (Apr. 2010): 243-9.

Raag et al., "Single-chain Fvs." FASEB J., Jan. 1995, vol. 9, No. 1, pp. 73-80.

Rudikoff et al., Proc. Natl. Acad. Sci. USA 79 (1982): 1979.

Sirk et al., "Site-specific, thiol-mediated conjugation of fluorescent probes to cysteine-modified diabodies targeting CD20 or HER2." Bioconjug Chem. 19.12 (Dec. 2008): 2527-34.

Stimmel et al., "Site-Specific Conjugation on Serine Cysteine Variant Monoclonal Antibodies." The Journal of Biological Chemistry 275. 39 (Sep. 29, 2000): 30445-30450.

Tai et al., "Targeting c-erbB-2 expressing tumors using single-chain Fv monomers and dimers." Cancer Res. 55.23Suppl (Dec. 1, 1995):5983s-5989s.

Verhaar et al., "Technetium-99m Radiolabeling Using a Phage-Derived Single-Chain Fv with a C-Terminal Cysteine." The Journal of Nuclear Medicine 37.5 (May 1996): 868-872.

Veri et al., "Therapeutic control of B cell activation via recruitment of Fcgamma receptor IIb (CD32B) inhibitory function with a novel bispecific antibody scaffold." Arthritis Rheum. 62.7 (Jul. 2010): 1933-43.

Whitlow et al., "Multivalent Fvs: characterization of single-chain Fv oligomers and preparation of a bispecific Fv," Protein Engineering, Aug. 1994, vol. 7, No. 8, pp. 1017-1026.

Wu et al., "Anti-carcinoembryonic Antigen (CEA) Diabody for Rapid Tumor Targeting and Imaging." Tumor Targeting 4 (1999): 47-58.

Wu et al., "High-resolution MicroPET Imaging of Carcino-Embryonic Antigen-Positive Xenografts By Using a Copper-64-Laeled Engineered Antibody Fragment," Proc. Natl. Acad. Sci. USA, vol. 97, o. 15, pp. 8495-8500 (2000).

Wu et al.,"Tumor localization of Anti-CEA Single-Chain Fvs: Improved Targeting by Non-Covalent Dimers," Immunotechnology, vol. 2, pp. 21-36 (1996).

Yazaki et al., "Mammalian Expression and Hollow Fiber Bioreactor Production of Recombinant Anti-CEA Diabody and Minibody for Clinical Applications." Journal of Immunological Methods 253 (2001): 195-208.

Yazaki et al., "Tumor Targeting of Radiometal Labeled Anti-CEA Recombinant T84.66 Diabody and T84.66 Minibody: Comparision to Radioiodinated Fragments." Bioconjuqate Chem. 12 (2001): 220-228.

You et al., "Expression, Purification, and Characterization of a Two Domain Carcinoembryonic Antigen Minigen (N-A3) in Pichia Pastoris:The Essential Role of the N-Domain." Anticancer Research 18 (1998): 3193-3202.

City of Hope National Medical Center, "Anti-CEA antibody T84.66 humanized," Medical Imaging Law Weekly, copyright 2004, http://www.newsrx.com/newsletters/Medical-Imaging-Law-Weekly; dated for online publication Nov. 27, 2004.

(56) References Cited

OTHER PUBLICATIONS

George et al., "Radiometal labeling of recombinant proteins by a genetically engineered minimal chelation site: technetium-99m coordination by single-chain Fv antibody fusion proteins through a C-terminal cysteinyl peptide," Proc. Natl. Acad. Sci. USA, Aug. 1995, vol. 92, No. 18, pp. 8358-8362.

Gu et al., "Biological activity and microPET imaging properties of chimeric and humanized anit-prostate stem cell antigen (PSCA) antibodies," Proc Amer Assoc Cancer Res., 2005, vol. 46, Abstract #696 [Retrieved on May 14, 2012], URL: http://aacrmeetingabstracts.org/cgi/content/abstract/2005/1/164-b.

Marty et al., "Production of functionalized single-chain Fv antibody fragments binding to the ED-B domain of the B-isoform of fibronectin in *Pichia pastoris*," Protein Expression and Purification, Feb. 2001, vol. 21, Issue 1, pp. 156-164.

Neumaier et al., "Cloning of the genes for T84.66, and antibody that has a high specificity and affinity for carcinoembryonic antigen, and expression of chimeric human/mouse T84.66 genes in myeloma and Chinese hamster ovary cells," Cancer Research, 1990, vol. 50, pp. 2128-2134.

Preliminary Amendment filed on Dec. 21, 2011 in U.S. Appl. No. 12/788,477 (Filing Date: May 27, 2012) in 9 pages.

Urva et al., "Physiologically based pharmacokinetic (PBPK) model for T.84.66, a monoclonal anti-CEA antibody," Am. Assoc. Pharm. Sci. 10 (Supp. 2), 2008, pp. 957.

File History of U.S. Appl. No. 10/690,990, filed Oct. 23, 2003.

File History of U.S. Appl. No. 12/788,477, filed May 27, 2010.

File History of U.S. Appl. No. 13/554,306, filed Jul. 20, 2012.

Adams et al., "Prolonged in vivo tumour retention of a human diabody targeting the extracellular domain of human *HER2/neu*", British Journal of Cancer (1998) 77(9), 14051412.

Albrecht, H. et al., "Production of Soluble ScFvs with C-Temninal-Free Thiol for Site-Specific Conjugation or Stable Dimeric ScFvs on Demand," *Bioconjugate Chemistry*, 2004, vol. 15, no. 1, pp. 16-26.

Ballou, B. et al., "Noninvasive Imaging of Quantum Dots in Mice," *Bioconjugate Chem.*, 2004, vol. 15, pp. 79-86.

Bruchez, Jr., M. et al., "Semiconductor Nanocrystals as Fluorescent Biological Labels," Science, Sep. 25, 1998, vol. 281, pp. 2013-2016.

Carmichael, Ja et al., "The Crystal Structure of an Anti-CEA scFV Diabody Assembled from T84.66 scFvs in VL-to-VH Orientation: Implications for Diabody Flexibility," *J. Mol. Biol.*, 2003, vol. 326, pp. 341-351.

Chan, W.C. et al., "Quantum Dot Bioconjugates for Ultrasensitive Nonisotopic Detection," *Science*, Sep. 25,1998, vol. 281, pp. 2016-2018.

Fountaine, T.J. et al., "Multispectral imaging of clinically relevant cellular targets in tonsil and lymphoid tissue using semiconductor quantum dots," *Modem Pathology*, 2006, vol. 19, pp. 1181-1191.

Galfre, G. et al., "Preparation of Monoclonal Antibodies: Strategies and Procedures," *Methods in Enzymology*, 1981, vol. 73, pp. 3-46.

Gao, X. et al., "*In vivo* cancer targeting and imaging with semiconductor quantum dots," *Nature Biotechnology*, Aug. 2004, vol. 22, no. 8, pp. 969-976.

Gu, Z. et al., "Prostate stem cell antigen (PSCA) expression increases with high gleason score, advanced stage and bone metastasis in prostate cancer," *Oncogene*, 2000, vol. 19, pp. 1288-1296.

Gu, Z. "Biological activity and microPET imaging properties of chimeric and humanized anti-prostate stem cell antigen (PSCA) antibodies" *Biological Abstracts*, vol. 46, Abstract No. 696 (2005).

Holliger, P. et al., "Diabodies': Small bivalent and bispecific antibody fragments," *Proc. Natl. Acad. Sci. USA*, Jul. 1993, vol. 90, pp. 6444-6448.

Hollinger et al., "Engineered Antibody Fragments and the Rise of Single Domains", *Nature Biotechnology* (Nature Publishing Group, NY, NY, USA), vol. 23, No. 9 (2005) pp. 1126-1136.

Howarth, M. et al., "Targeting quantum dots to surface proteins in living cells with biotin ligase," *PNAS*, May 24, 2005, vol. 102, No. 21, pp. 7583-7588.

Hu, S-Z. et al., "Minibody: A Novel Engineered Anti-Carcinoembryonic Antigen Antibody Fragment (Single-Chain Fv-CH3) Which Exhibits Rapid, High-Level Targeting of Xenografts," *Cancer Research*, (1996).

Jaiswal, J.K. et al., "Long-term multiple color imaging of live cells using quantum dot bioconjugates," *Nature Biotechnology*, Jan. 2003, vol. 21, pp. 47-51.

Jaiswal, J.K. et al., "Use of quantum dots for live cell imaging," *Nature Methods*, Oct. 2004, vol. 1, No. 1, pp. 73-78.

Kenanova, V. et al., "Tailoring antibodies for radionuclide delivery," *Expert Opin. Drug Deliv.*, 2006, vol. 3, No. 1, pp. 53-70.

Kim, S. et al., "Near-infrared fluorescent type II quantum dots for sentinel lymph node mapping," *Nature Biotechnology*, Jan. 2004, vol. 22, no. 1, pp. 93-97.

Leyton et al. "Anti-Prostate Sem Cell antigen (PSCA) Antibody Fragments for Pet Imaging of Prostate Cancer," *Cancer Biotherapy & Radiopharnaceulcals* (Mary Ann Liebert, USA), vol. 21, No. 4 (2006) p. 391.

Li, L. et al., "Reduction of Kidney Uptake in Radiometal Labeled Peptide Linkers Conjugated to Recombinant Antibody Fragments. Site Specific Conjugation of DOTA-Peptides to a Cys-Diabody," *Bioconjugate* Chem., 2002, vol. 13, No. 5, pp. 985-995.

Maysinger, D. et al., "Real-Time Imaging of Astrocyte Response to Quantum Dots: In Vivo Screening Model System for Biocompatibility of Nan Dparticles," *Nano Letters*, 2007, vol. 7, No. 8, pp. 2513-2520.

Medintz, I.L. et al., "Self-assembled nanoscale biosensors based on quantum dot FRET donors," *Nature Materials*, Sep. 2003, vol. 2, pp. 630-638.

Michalet, X. et al., "Quantum Dots for Live Cells, in Vivo Imaging, and Diagnostics," *Science*, Jan. 28, 2005, vol. 307, pp. 538-544.

Olafsen, T. et al., "Covalent disulfide-linked anti-CEA cliabody allows site-specific conjugation and radiolabeling for tumor targeting applications," *Protein Engineering, Design & Selection*, 2004, vol. 17, No. 1, pp. 21-27.

Olafsen et al. "Targeting, imaging, and therapy using a humanized antiprostate stem cell antigen (PSCA) antibody," *Journal of Immunotherapy* (Lippincott 'Williams & Wilkins, Hagerstown, MD., USA), vol. 30 No. 4 (2007) pp. 396-405.

Olafsen, T. et al., "Optimizing Radiolabeled Engineered Anti_p185HER2 Antibody Fragments for *In vivo* Imaging," Cancer Research, Jul. 1, 2005, vol. 65, No. 13, pp. 5907-5916.

Saffran et al., "Anti-PSCA MABS Inhibit Tumor Growth and Metastasis Formation and Prolong the Survival of Mice Bearing Human Prostate Cancer Xenografts," *Proceedings of the National Academy of Sciences of the United States (PNAS), National Academy of Science, US*, vol. 98, No. 5 (2001) pp. 2658-2663.

Smith, B.R. et al., "Real-Time Intravital Imaging of RGD-Quantum Dot Binding to Luminal Endothelium in Mouse Tumor Neovasculature," *Nano Letters*, Sep. 2008, vol. 8, No. 9, pp. 2599-2606.

So, M-K. et al., "Self-illuminating quantum dot conjugates for *in vivo* imaging," *Nature Biotechnology*, Mar. 2006, vol. 24, no. 3, pp. 339-343.

Stroh, M. et al., "Quantum dots spectrally distinguish multiple species within the tumor milieu *in vivo*," *Nature Medicine*, Jun. 2005, vol. 11, No. 6, pp. 678-682.

Sundaresan, G. et al., "$^{124}$I-Labeled Engineered Anti-CEA Minibodies and Diabodies Allow High-Contrast, Antigen-Specific Small-Animal PET Imaging of Xenografts in Athymic Mice," *The Journa/ofNuclearMedicine*, Dec. 2003, vol. 44, No. 12, pp. 1962-1969.

Tada, H. et al., "*In vivo* Real-time Tracking of Single Quantum Dots Conjugated with 29. Monoclonal Anti-HER2 Antibody in Tumors of Mice," *Cancer Research*, Feb. 1, 2007, vol. 67, No. 3, pp. 1138-1144.

Voura, E.B. et al., "Tracking metastatic tumor cell extravasation with quantum dot 30. nanocrystals and fluorescence emission-scanning microscopy," *Nature Medicine*, Sep. 2004, vol. 10, No. 9, pp. 993-998.

Wu, A.M. et al., "High-Resolution MicroPET Imaging of Carcinoembryonic Antigen-Positive Xenografts by Using a Copper-64-Labeled Engineered Antibody Fragment," *PNAS*, (2000), vol. 97, No. 15, pp. 8495-8500.

(56) References Cited

OTHER PUBLICATIONS

Wu, A.M. et al., "Anti-carcinoembryonic antigen (CEA) diabody for rapid tumor targeting and imaging," *Tumor Targeting*, 1999, vol. 4, pp. 47-58.

Wu, X. et al., "Immunofluorescent labeling of cancer marker Her2 and other cellular targets with semiconductor quantum dots," *Nature Biotechnology*, Jan. 2003, vol. 21, pp. 41-46.

Xing, Y. et al., "Bioconjugated quantum dots for multiplexed and quantitativ immunohistochemistry," *Nature Protocols*, 2007, vol. 2, No. 5, pp. 1152-1165.

Yazaki, P.J. et al., "Mammalian expression and hollow fiber bioreactor production of 34. recombinant anti-CEA diabody and minibody for clinical applications," *Journal of Immunological Methods*, 2001, vol. 253, pp. 195-208.

Yokota, T. et al., "Rapid Tumor Penetration of a Single-Chain Fv and Comparison with Other Immunoglobulin Forms," *Cancer Research*, Jun. 15, 1992, vol. 52, pp. 3402-3408.

Fig. 1 (sheet 1)

```
tctagagccgccaccatggagacagacacactcctgctatgggtgctgtctctggtt
        S  R  A  A  T  M  E  T  D  T  L  L  L  W  V  L  L  W  V
        signal peptide
ccaggttccaccggtgacattcagctgacccatcctcaagctctttgtccgcctctgtg
        P  G  S  T  G  D  I  Q  L  T  Q  S  P  S  S  L  S  A  S  V
                                VL
ggggataggtcaccatcacctgcagtgccagttcaagtgtaagattcattcactggtac
        G  D  R  V  T  I  T  C  S  A  S  S  S  V  R  F  I  H  W  Y
cagcagaaaccaggaaaagctcccaaaagactcatctatgacacatccaaactggcttct
        Q  Q  K  P  G  K  A  P  K  R  L  I  Y  D  T  S  K  L  A  S
ggcgtcccttctaggttcagtggcagtggatctgggacagacttcacctcaccattagc
        G  V  P  S  R  F  S  G  S  G  S  G  T  D  F  T  L  T  I  S
agtctgcagccggaagatttcgccacctattactgtcagcagtggagtagtagcccattc
        S  L  Q  P  E  D  F  A  T  Y  Y  C  Q  Q  W  S  S  S  P  F
acgttcggacaggggaccaaggtggagataaaaggcagtactagcggcggtggctccgga
        T  F  G  Q  G  T  K  V  E  I  K  G  S  T  S  G  G  G  S  G
```

Fig. 1 (sheet 2)

```
                                    linker
ggcggctccggaggtggcggcagctcagaggttcagaggttcagctgtggagtctgggtggcctt
 G  G  S  G  G  G  G  S  S  E  V  Q  L  V  E  S  G  G  L
                    VH
gtgcagccaggggctcactccgtttgtcctgcgcagcttctgcttcaacattaaagac
 V  Q  P  G  G  S  L  R  L  S  C  A  A  S  G  F  N  I  K  D
tactatatacactgggtgcgtcaggctcaggcccctgtaaggctggaatgggttgcatggatt
 Y  Y  I  H  W  V  R  Q  A  P  G  K  G  L  E  W  V  A  W  I
gatcctgagaatggtgacactgaatttgtcccgaagttccaggcagatgaacagcctgccactataagc
 D  P  E  N  G  D  T  E  F  V  P  K  F  Q  G  R  A  T  I  S
gcagacacatccaaaaacacagcctacctgcagatgaacagcctgcgtgctgaggacact
 A  D  T  S  K  N  T  A  Y  L  Q  M  N  S  L  R  A  E  D  T
gccgtctattattgtaaaacgggggttctggggtcaaggaaccctggtcaccgtctccg
 A  V  Y  Y  C  K  T  G  F  W  G  Q  G  T  L  V  T  V  S
agcgagcccaaatcttgtgacaaaactcacacatgcccaccgtgcccaggtaagctct
 S  E  P  K  S  C  D  K  T  H  T  C  P  P  C  G  G  G  S  S
```

Fig. 1 (sheet 3)

```
hinge                                                              extension
ggcggtggatccggcgggcagcccgagaaccacaggtgtacaccctgcccccatcccgg
 G  G  G  S  G  G  Q  P  R  E  P  Q  V  Y  T  L  P  P  S  R
                   CH3
gatgagctgaccaagaaccaggtcagcctgacctgcctggtcaaaggcttctatcccagc
 D  E  L  T  K  N  Q  V  S  L  T  C  L  V  K  G  F  Y  P  S
gacatcgccgtggagtgggagagcaatgggcagccggagaacaactacaagaccacgcct
 D  I  A  V  E  W  E  S  N  G  Q  P  E  N  N  Y  K  T  P
cccgtgctggactccgacggctccttcttcctctacagcaagctcaccgtggacaagagc
 P  V  L  D  S  D  G  S  F  F  L  Y  S  K  L  T  V  D  K  S
aggtggcagcaggggaacgtcttctcatgctccgtgatgcatgaggctctgcacaaccac
 R  W  Q  Q  G  N  V  F  S  C  S  V  M  H  E  A  L  H  N  H
tacacgcagaagagcctctccctgtctccgggtaaatgatag
 Y  T  Q  K  S  L  S  L  S  P  G  K  -  -
```

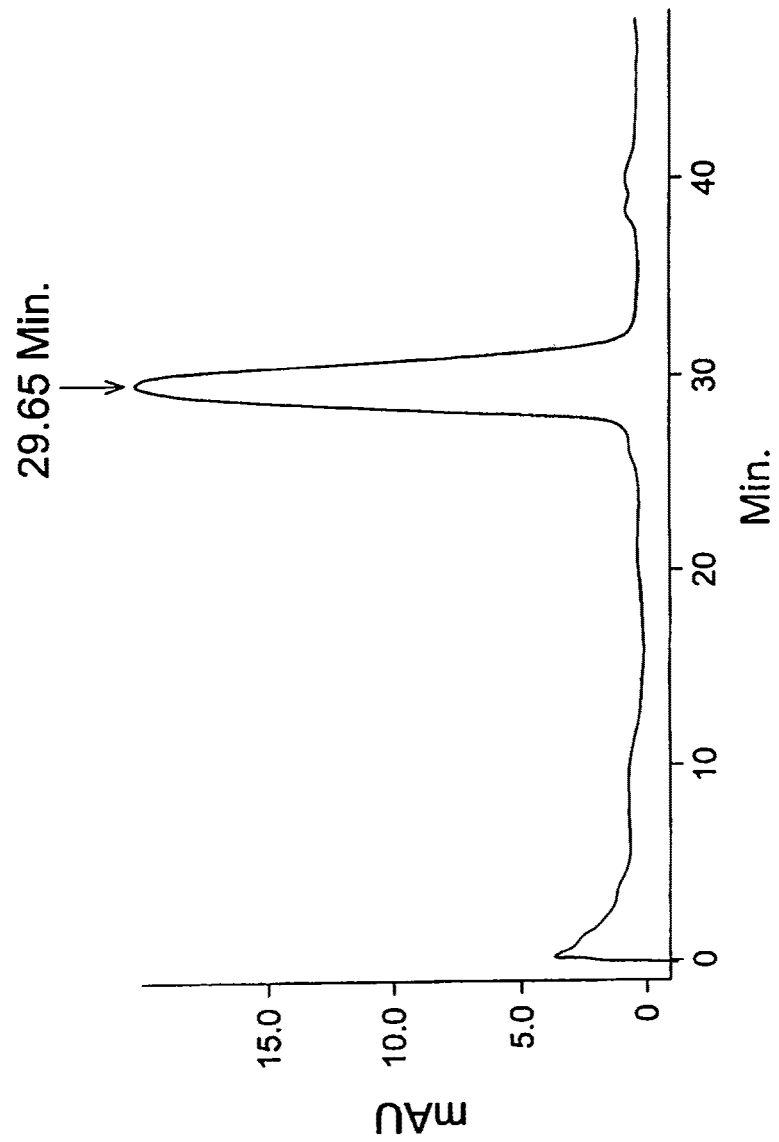

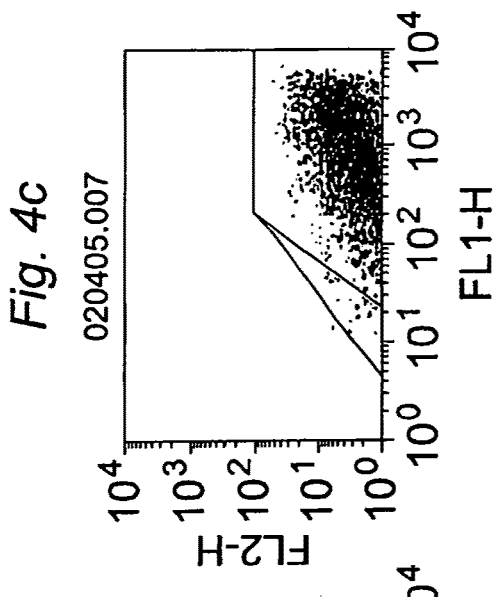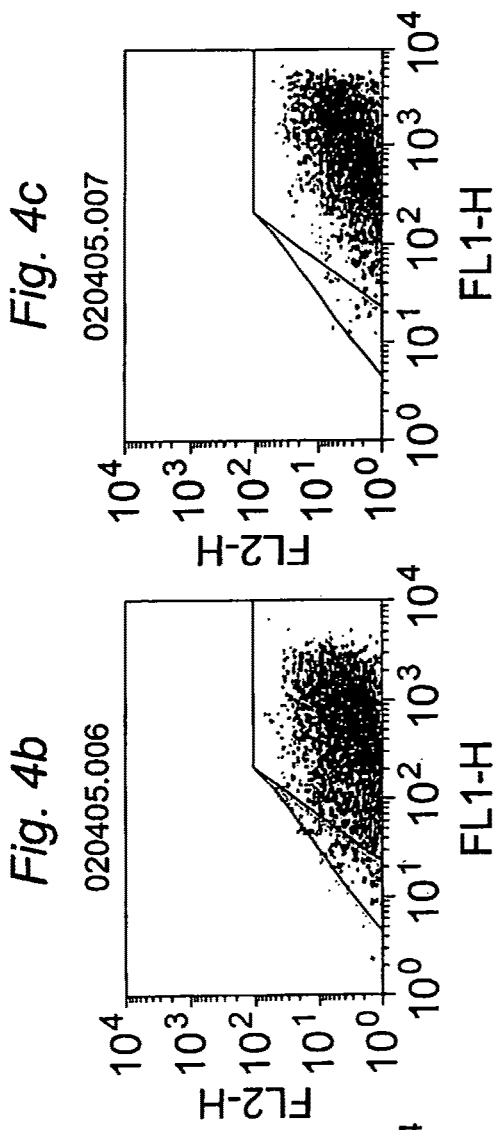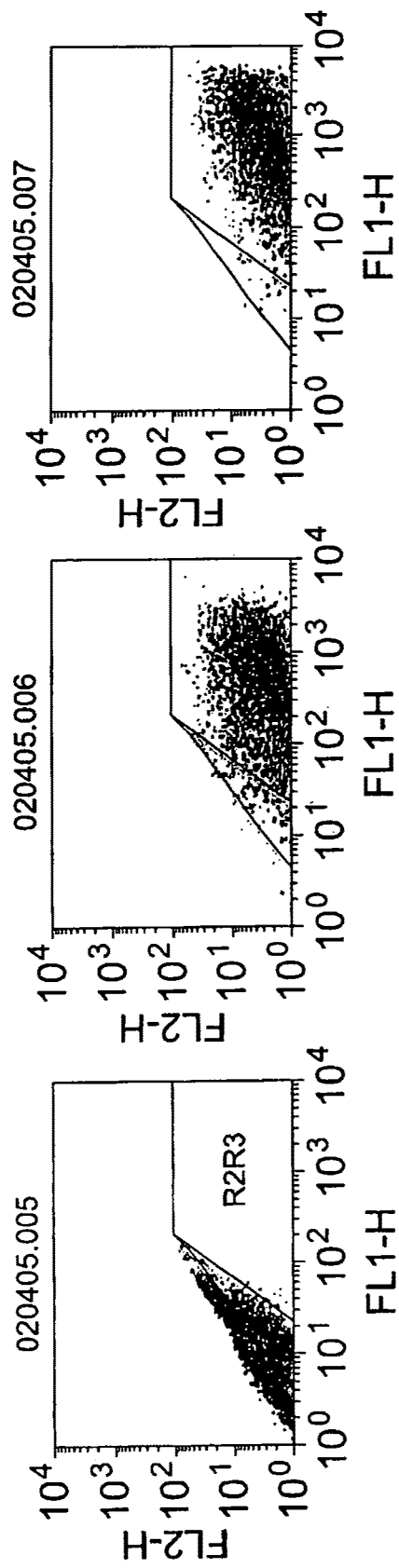

Engineering antibody fragments to control PK

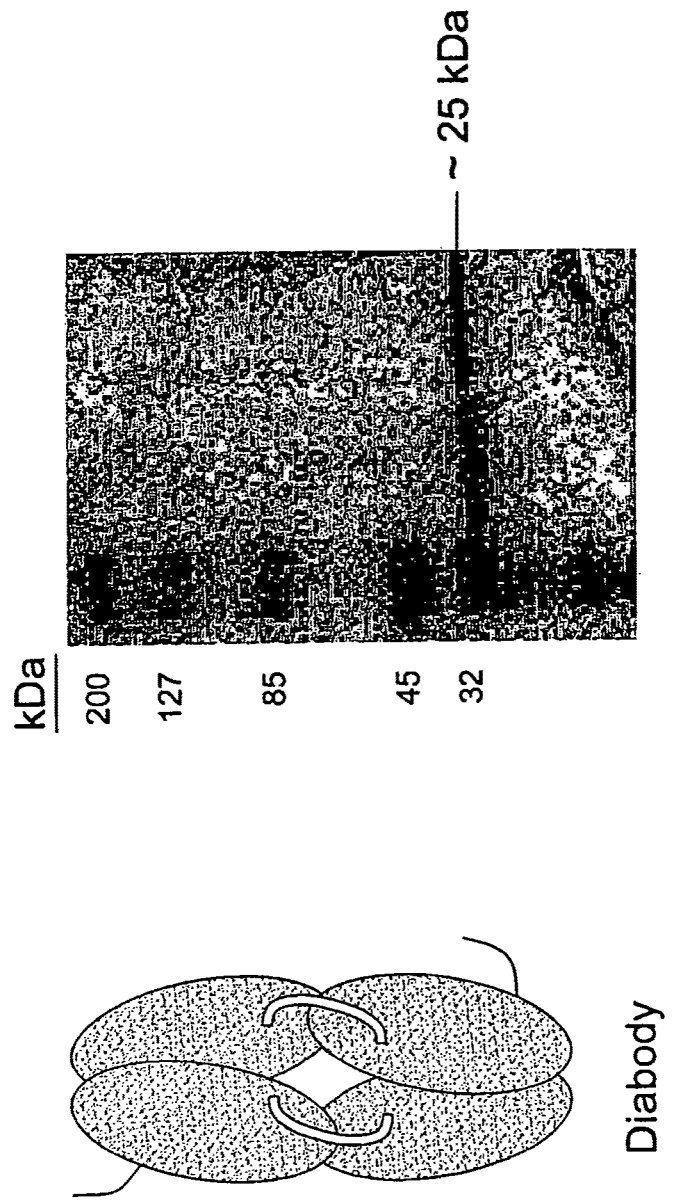
Fig. 8 (sheet 1)
Humanized Anti-PSCA Diabodies: Expression and Characterization

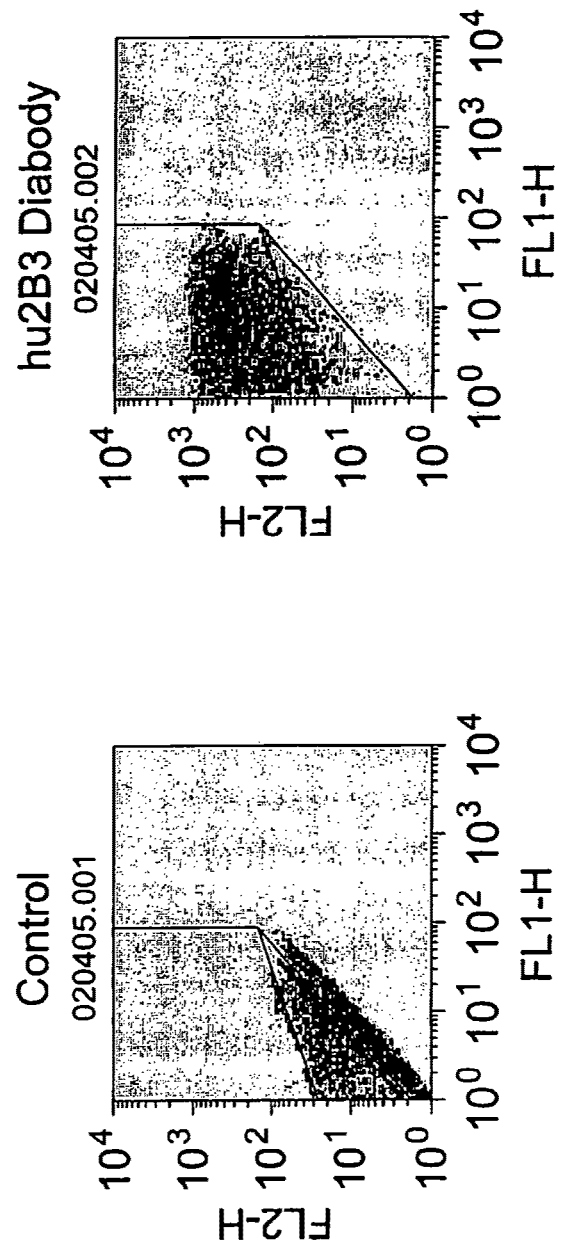
Fig.8 (sheet 2)
Binding of hu2B3 diabody to PSCA-positive cells by flow cytometry Fig. 9 (sheet 1)
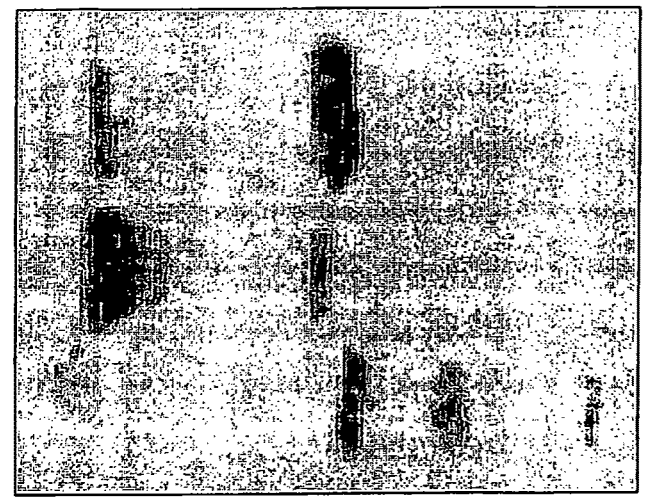
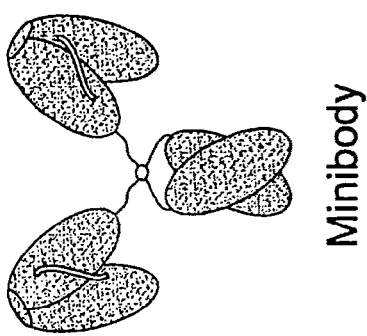
Minibody
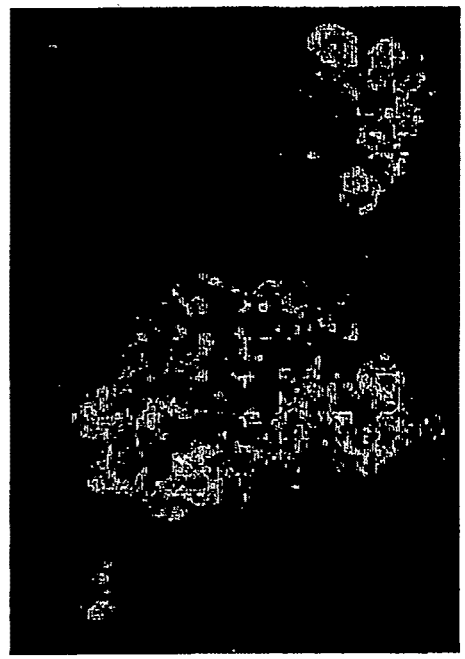

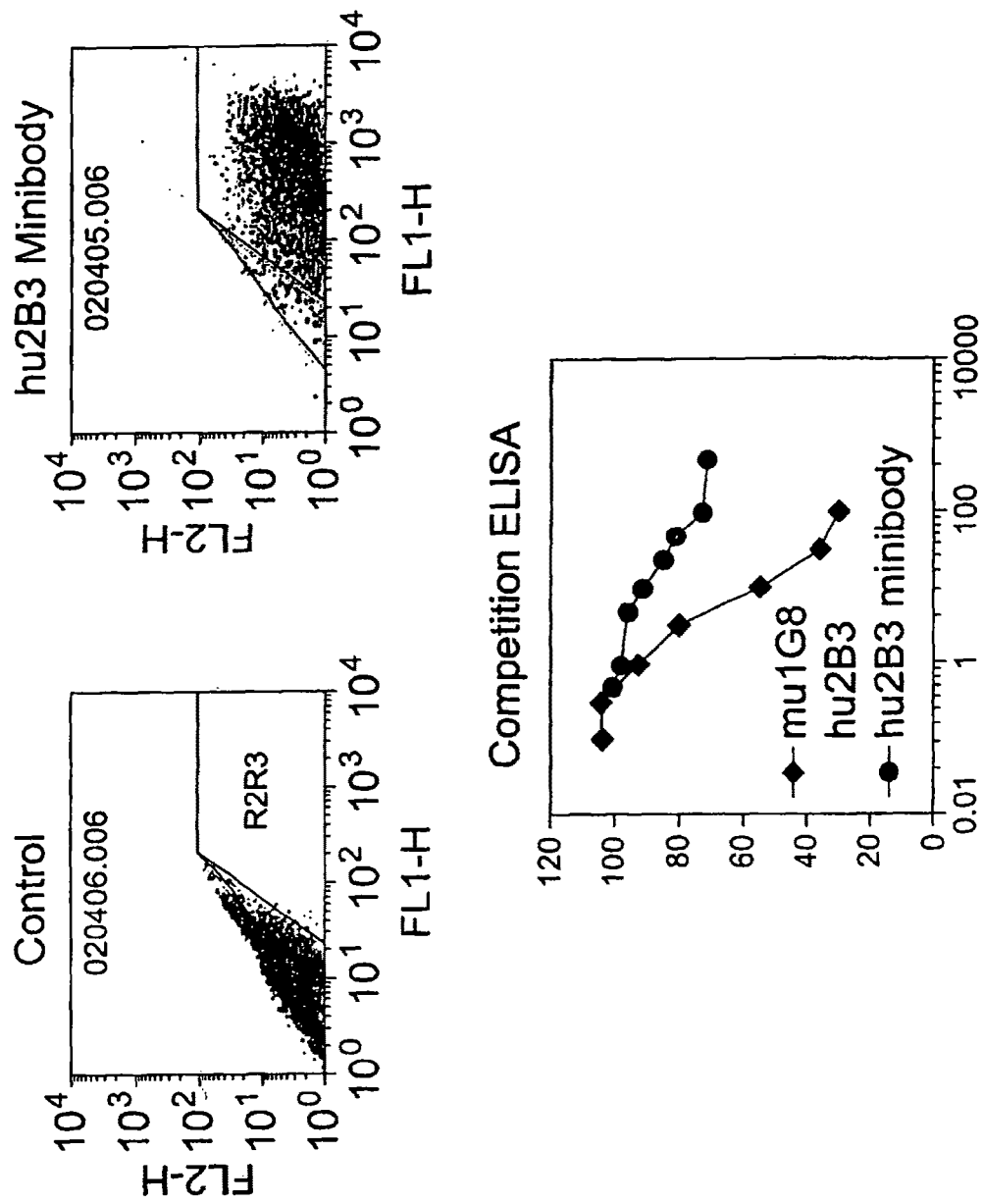
Fig. 9 (sheet 2)

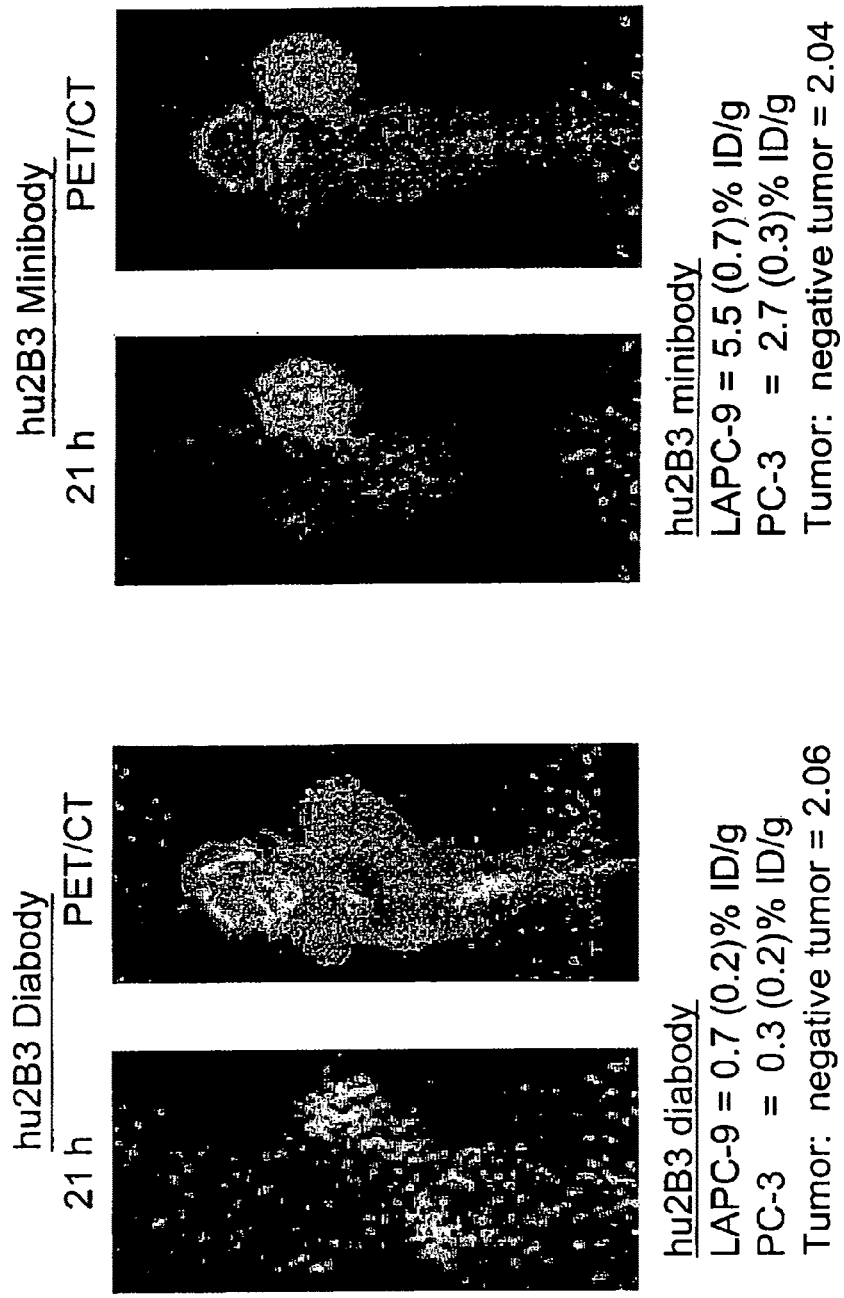

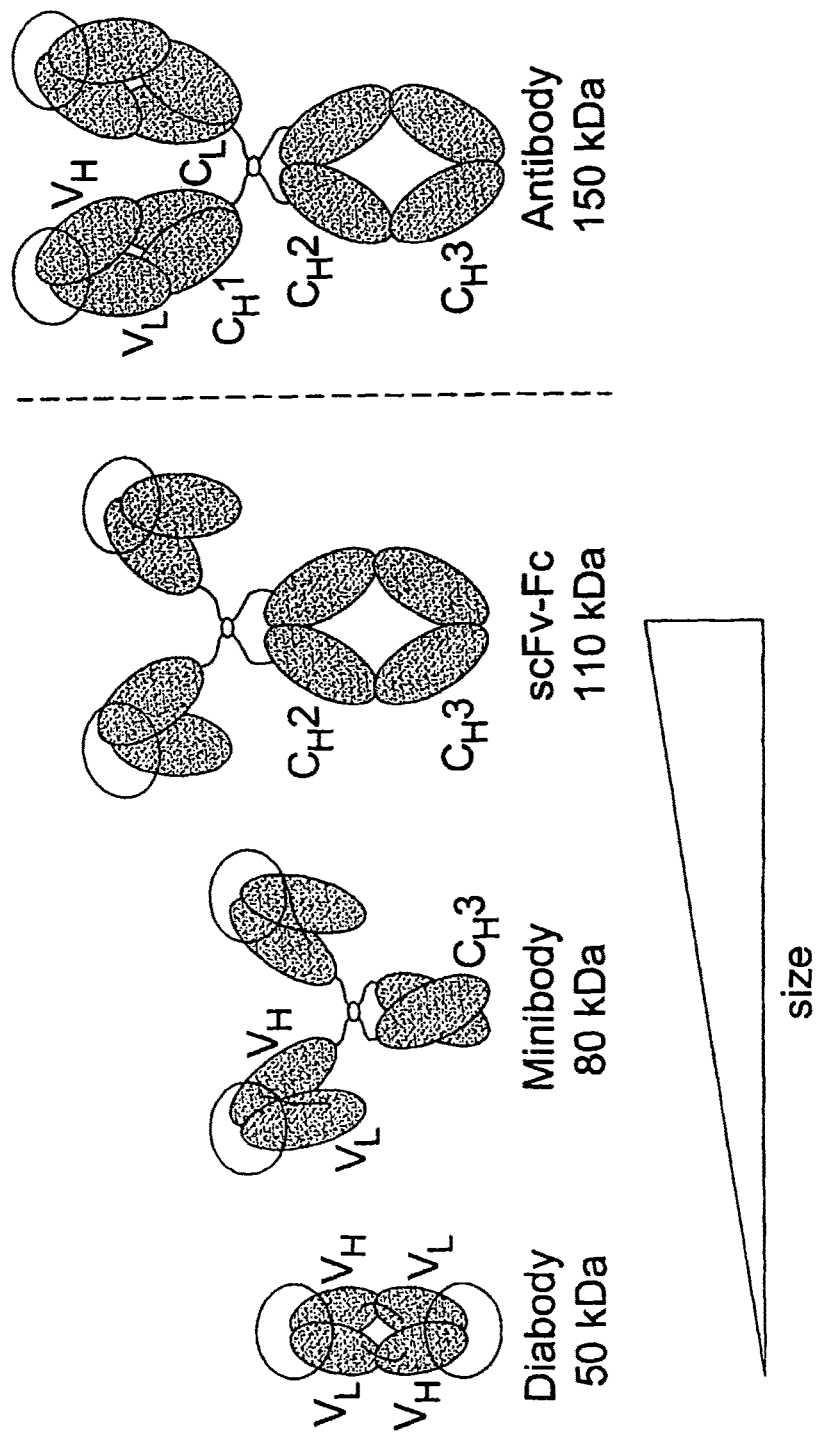

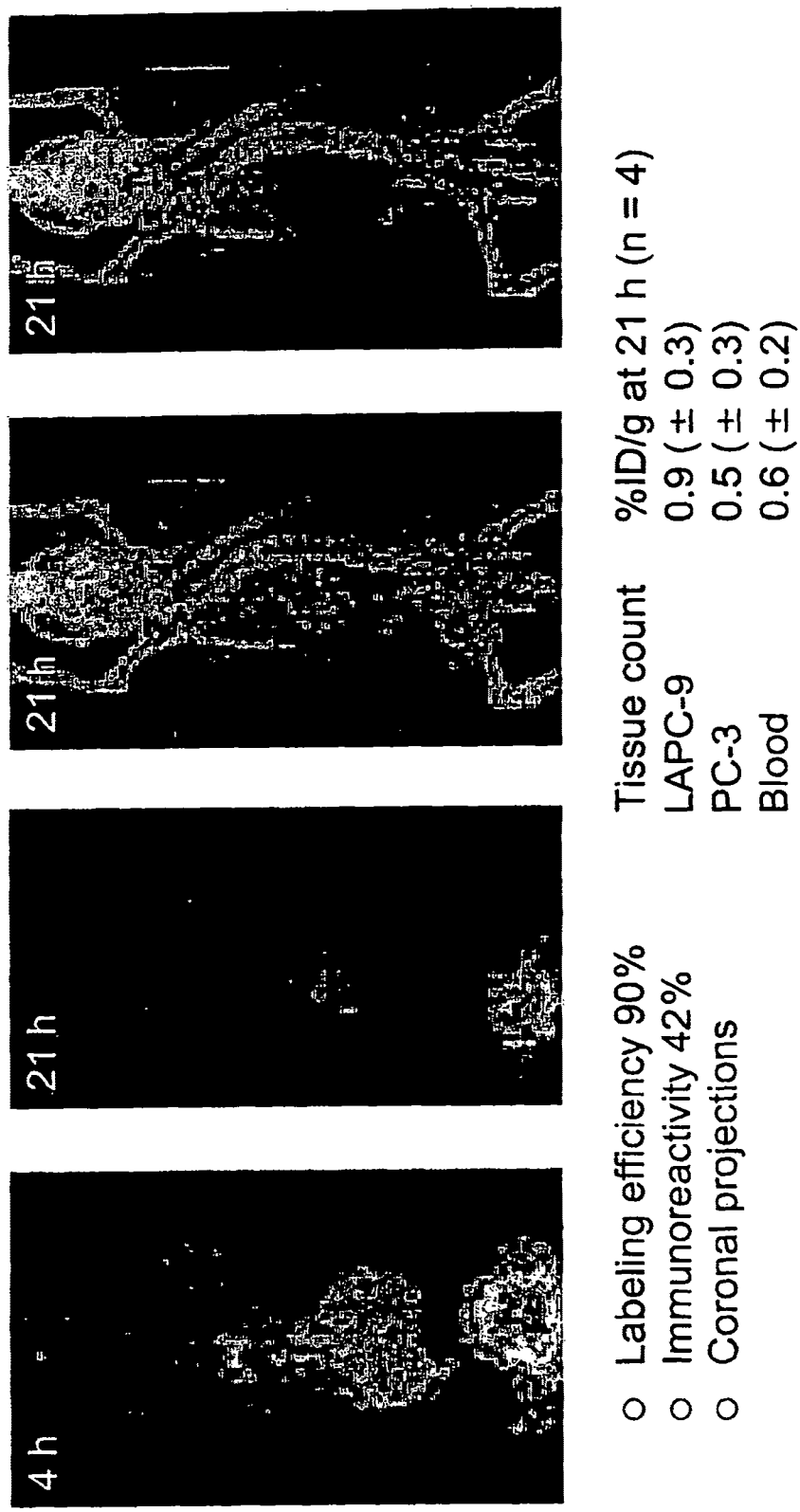

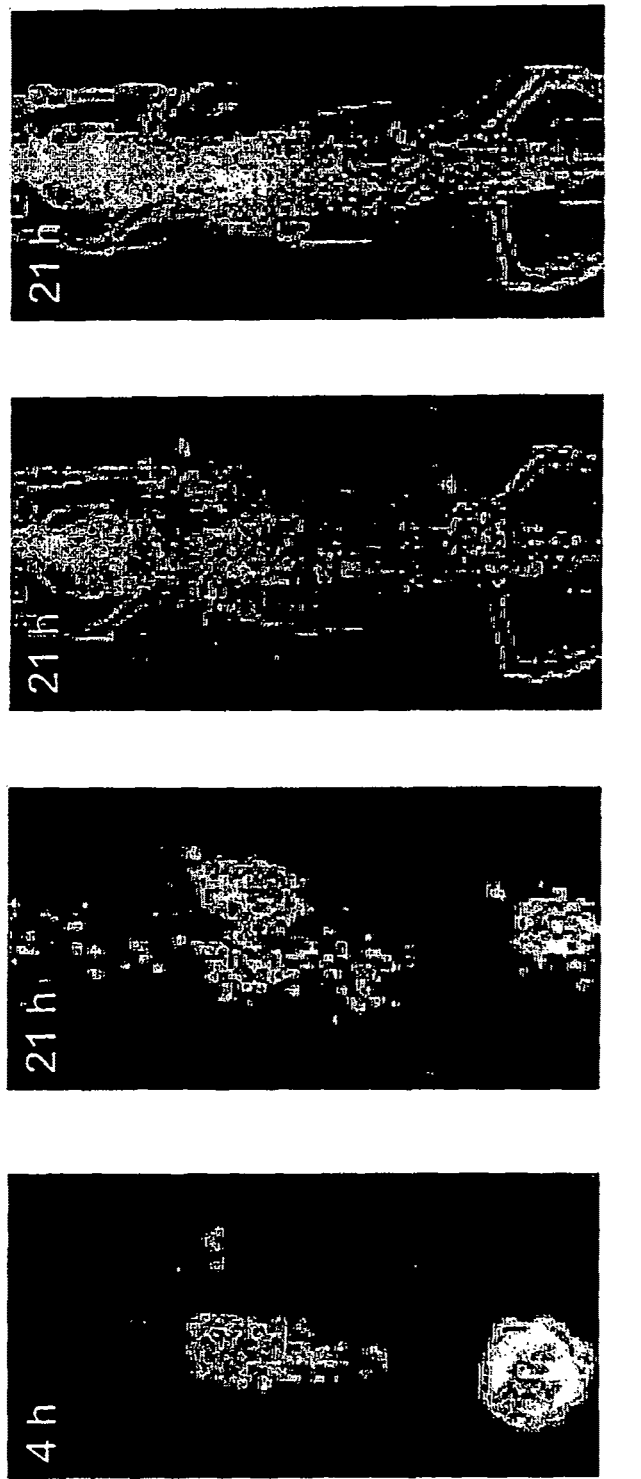
Fig. 12 (sheet 1)
anti-PSCA Minibody: I-124
microPET imaging
○ Labeling efficiency 84%
○ Immunoreactivity 34%
○ Coronal projections

Fig. 12 (sheet 2)

I-124 21 h Biodistribution

| Organ | Minibody n = 12 | Deactivated Minibody n = 12 | |
|---|---|---|---|
| | %ID/g | %ID/g | |
| LAPC-9 (+) | 5.2 (±1.6) | 1.5 (±0.6) | 3.5 |
| PC-3 (-) n = 4 | 2.6 (±0.2) | -- | 2.0 |
| Liver | 1.3 (±0.3) | 1.0 (±0.2) | |
| Spleen | 1.5 (±0.5) | 0.9 (±0.3) | |
| Kidney | 1.9 (±0.5) | 1.5 (±0.3) | |
| Lung | 3.4 (±1.0) | 2.1 (±0.4) | |
| Blood | 4.9 (±1.3) | 4.4 (±0.5) | |
| Carcass | 1.2 (±0.1) | -- | |

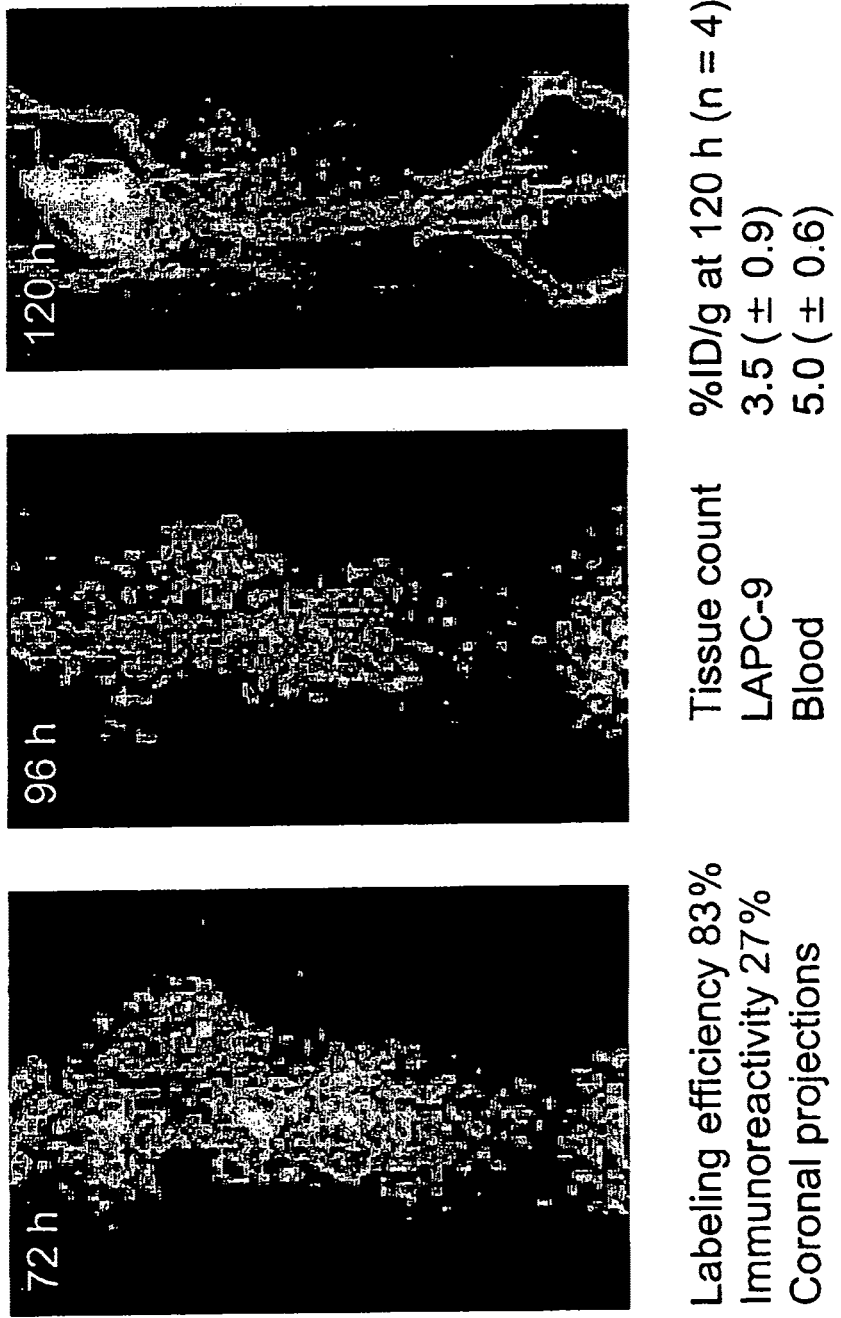

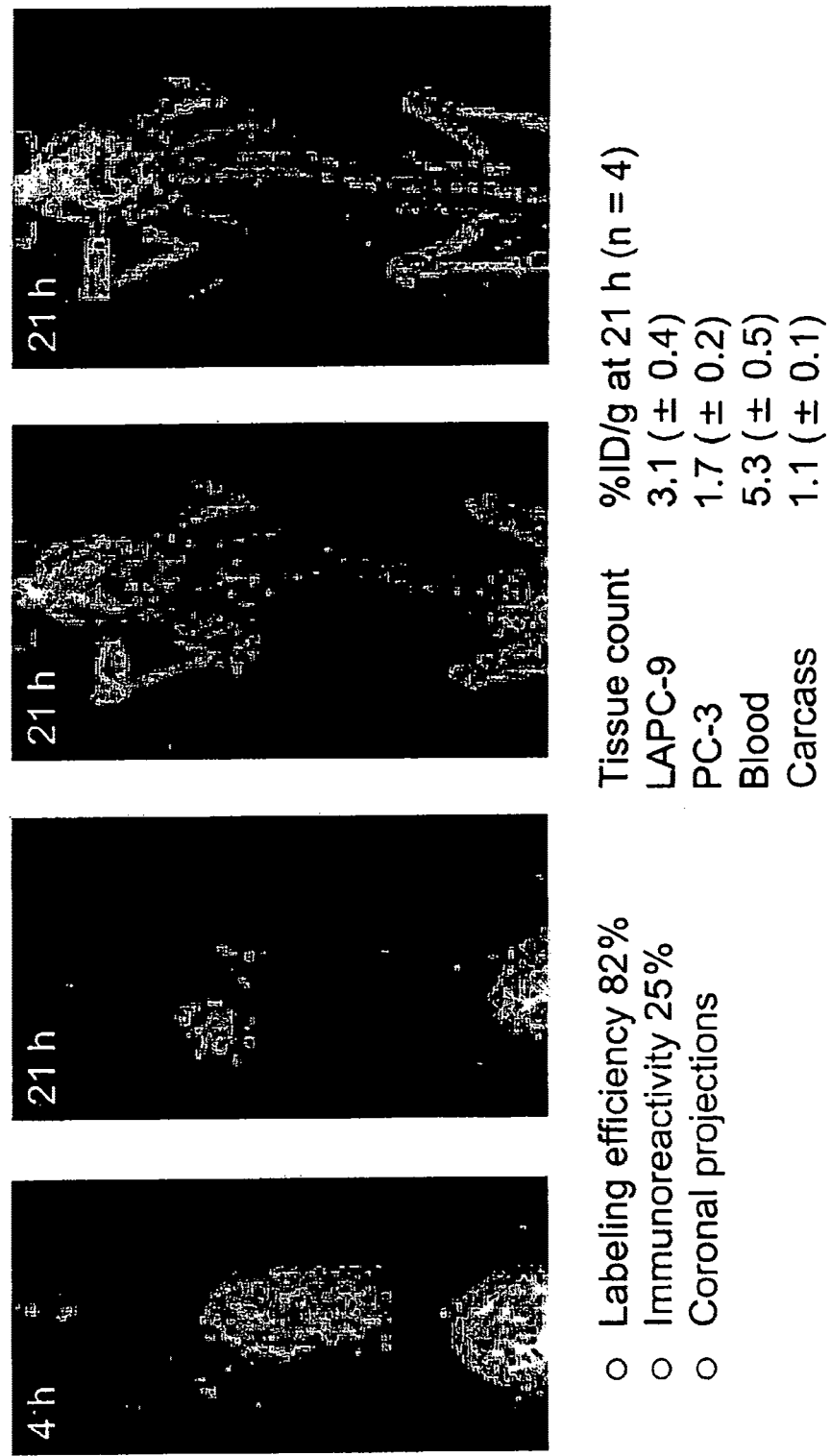
Fig. 13 (sheet 2)
anti-PSCA scFv-Fc (double mutant, rapid clearing) microPET imaging
○ Labeling efficiency 82%
○ Immunoreactivity 25%
○ Coronal projections
| Tissue count | %ID/g at 21 h (n = 4) |
|---|---|
| LAPC-9 | 3.1 (± 0.4) |
| PC-3 | 1.7 (± 0.2) |
| Blood | 5.3 (± 0.5) |
| Carcass | 1.1 (± 0.1) |

ENGINEERED ANTI-PROSTATE STEM CELL ANTIGEN (PSCA) ANTIBODIES FOR CANCER TARGETING

CROSS-REFERENCES TO RELATED APPLICATIONS

The present application claims priority to U.S. Provisional Patent Application No. 60/784,192, filed on Mar. 20, 2006, the disclosure of which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant Nos. PO1 CA 43904 and P50 CA 92131, awarded by the NIH/NCI. The U.S. Government has certain rights in this invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Prostate cancer is the second leading cause of cancer deaths in men, with approximately 27,000 deaths and 234,000 new cases expected this year in American men. Prostate cancer arises in the prostate, an approximately walnut-sized gland found in the male reproductive system which is responsible for the generation and storage of seminal fluid. The prostate contains many small glands which make about twenty percent of the fluid comprising semen. In prostate cancer, the cells of these prostate glands are transformed into cancer cells. Because the prostate surrounds part of the urethra, prostate diseases often affect urination, ejaculation, or defecation.

Because prostate cancer begins when normal semen-secreting prostate gland cells undergo transformation into cancer cells, prostate cancer is classified as an adenocarcinoma, or glandular cancer. The region of the prostate gland where the adenocarcinoma is most common is the peripheral zone. Initially, small clumps of cancer cells remain confined to otherwise normal prostate glands, resulting in a condition known as carcinoma in situ or prostatic intraepithelial neoplasia (PIN). Over time, these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer most commonly metastasizes to the bones, lymph nodes, rectum, and bladder.

Screening for prostate cancer generally involves either digital rectal examination or prostate specific antigen (PSA) test. During a digital rectal examination, the health care provider checks the size, shape, and texture of the prostate for areas which are irregular, hard or lumpy, which may be indicative of prostate cancer. The PSA test measures the blood level of prostate-specific antigen, an enzyme produced by the prostate. PSA levels under 4 ng/mL are generally considered normal; PSA levels between 4 and 10 ng/mL indicate a risk of prostate cancer higher than normal, but the risk does not seem to rise within this six-point range. When the PSA level is above 10 ng/mL, the association with cancer becomes stronger.

While the measurement of serum PSA assay has proven to be a very useful diagnostic tool, the utility of the PSA test has limitations. For instance, PSA testing is not able to reliably identify early-stage disease. Similarly, there is no marker available for predicting the emergence of the typically fatal metastatic stage of the disease. Diagnosis of metastatic prostate cancer is achieved by open surgical or laparoscopic pelvic lymphadenectomy, whole body radionuclide scans, skeletal radiography, and/or bone lesion biopsy analysis. Clearly, better imaging and other less invasive diagnostic methods offer the promise of easing the difficulty those procedures place on a patient, as well as improving therapeutic options. Accordingly, there is a need for reagents that are capable of reliably identifying early-stage disease, predicting susceptibility to metastasis, and precisely imaging tumors to assist in the treatment, diagnosis, prognosis, and management of prostate cancer. The present invention satisfies these and other needs.

BRIEF SUMMARY OF THE INVENTION

This invention provides novel humanized antibody fragments that specifically bind prostate cell-surface antigen (PSCA) for use in the diagnosis of cancer, for providing a prognosis of cancer progression, and for cancer imaging, particularly of prostate, bladder, and pancreatic cancer.

In a first embodiment, the invention provides a humanized antibody fragment which specifically binds to PSCA on the surface of cancer cells. Examples of antibody fragments of this invention include a scFv, a scFv dimer (diabody), a sc-Fv-CH3 dimer (minibody), and a scFv-Fc, in which the antibody fragment comprises sequences of the variable light chain (VL) and variable heavy chain (VH) regions as shown in FIG. 1. In aspects of this embodiment, the scFv dimer can include two scFv monomers joined by a linker. Suitable linkers include peptide sequences, of which, the sequence [(GGGS)$_2$] (SEQ ID NO:3) is an advantageous example. In other aspects of this embodiment, the antibody fragment has an affinity of $K_D$=2.0 nM or less or $K_D$=5.5 nM or less. Advantageous antibody fragments for the practice of the invention include scFv dimers (diabodies) and sc-Fv-$C_H$3 dimer (minibodies).

In a second embodiment, this invention provides a method of diagnosing a cancer that overexpresses cell surface PSCA by (a) administering to a subject a humanized antibody fragment which specifically binds to PSCA on the surface of cancer cells, in which the antibody fragment can be a scFv, a scFv dimer (diabody), a sc-Fv-CH3 dimer (minibody), or a scFv-Fc, and (b) determining whether or not PSCA protein is overexpressed in the subject using molecular in vivo imaging, thus diagnosing the cancer that overexpresses cell surface PSCA. In an advantageous aspect, the antibody fragment comprises the sequences of variable light chain (VL) and variable heavy chain (VH) regions as shown in FIG. 1.

In a third embodiment, this invention provides a method of providing a prognosis for a cancer that overexpresses cell surface PSCA by (a) administering to a subject a humanized antibody fragment which specifically binds to PSCA on the surface of cancer cells, in which the antibody fragment can be a scFv, a scFv dimer (diabody), a sc-Fv-CH3 dimer (minibody), or a scFv-Fc, and (b) determining whether or not PSCA protein is overexpressed in the subject using molecular in vivo imaging, thus providing a prognosis for the cancer that overexpresses cell surface PSCA. In an advantageous aspect, the antibody fragment comprises the sequences of variable light chain (VL) and variable heavy chain (VH) regions as shown in FIG. 1.

In aspects of the second and third embodiments, the cancer that overexpresses cell surface PSCA includes prostate cancer, bladder cancer, and pancreatic cancer. In further aspects of the second and third embodiments, the humanized antibody fragment is linked to a detectable moiety. Examples of detectable moieties include a radionuclide, a nanoparticle, a fluorescent dye, a fluorescent marker, and an enzyme. Examples of detectable moieties that are radionuclides include $^{64}$Cu, $^{99m}$Tc, $^{111}$In, $^{123}$I, $^{124}$I or $^{131}$I. Among the molecular in vivo imaging methods that may be used in the practice of the second and third embodiments are MRI, SPECT, PET, and planar gamma camera imaging.

A fourth embodiment of the invention provides a method of providing a diagnosis or prognosis for a cancer that overexpresses cell surface PSCA by (a) contacting a biological sample with a humanized antibody fragment which specifically binds to PSCA on the surface of cancer cells, in which the antibody fragment can be a scFv, a scFv dimer (diabody), a sc-Fv-CH3 dimer (minibody), and a scFv-Fc, and the antibody fragment comprises the sequences of variable light chain ($V_L$) and variable heavy chain ($V_H$) regions as shown in FIG. 1; and (b) determining whether or not PSCA protein is overexpressed in the biological sample, thus providing a diagnosis or prognosis for the cancer that overexpresses cell surface PSCA.

In aspects of the fourth embodiment, the cancer that overexpresses cell surface PSCA includes prostate cancer, bladder cancer, and pancreatic cancer. In further aspects, the biological sample is a tissue biopsy or bodily fluid sample, of which, blood, urine, or prostatic fluid are examples. In some aspects of this embodiment, the humanized antibody fragment is linked to a detectable moiety, such as, a radionuclide, a nanoparticle, a fluorescent dye, a fluorescent marker, and an enzyme.

A fifth embodiment of the invention provides a method of treating or preventing a cancer that overexpresses cell surface PSCA in a subject by (a) administering to the subject a therapeutically effective amount of a humanized antibody fragment which specifically binds to PSCA on the surface of cancer cells, in which, the antibody fragment can be a scFv, a scFv dimer (diabody), a sc-Fv-CH3 dimer (minibody), and a scFv-Fc, and the antibody fragment comprises the sequences of variable light chain ($V_L$) and variable heavy chain ($V_H$) regions as shown in FIG. 1, thus treating or preventing a cancer that overexpresses cell surface PSCA in the subject. In some aspects of this embodiment, the cancer that overexpresses cell surface PSCA includes prostate cancer, bladder cancer, and pancreatic cancer.

BRIEF DESCRIPTION OF THE DRAWINGS

FIG. 1 shows the DNA sequence (SEQ ID NO:1) and translated protein sequence (SEQ ID NO:2) of a humanized anti-PSCA minibody. Also indicated are the beginnings of the following protein segments: signal peptide (for mammalian secretion), light chain variable region (VL) from the humanized 2B3 anti-PSCA antibody (SEQ ID NO:6), the 18 amino acid inter-domain linker peptide, heavy chain variable region (VH) from humanized 2B3 (SEQ ID NO:7), human IgG1 hinge sequence and 10 amino acid extension, and the human IgG1 CH3 domain followed by two stop codons.

FIG. 3 illustrates size-exclusion HPLC of anti-PSCA minibody showing homogenous peak at expected molecular size.

FIG. 4 illustrates flow cytometric binding studies of anti-PSCA minibody. Panel 1, antigen negative B-cell line; Panel 2, B-cell line stably transfected to express PSCA, Panel 3, PSCA-expressing LNCaP human prostate cancer cells.

FIG. 8 (left panel) shows a schematic representation of a humanized PSCA diabody of the invention and the migration of the diabody as a ~25 kDa protein on SDS-PAGE. The right panel shows the binding of the diabody to PSCA-positive cells by FACS.

FIG. 9 (left panel) shows a schematic representation of a humanized PSCA minibody of the invention and the migration of the minibody under reduced and non-reduced conditions on SDS-PAGE. Also shown is the binding of anti-PSCA minibody to antigen-positive cells by immunofluorescence microscopy. The right panel shows the binding of the minibody to PSCA-positive cells by FACS and a competitive ELISA assay using the minibody.

FIG. 10 shows co-registered microPET/microCT scans of a nude mouse bearing LAPC-9 (PSCA-positive human prostate cancer) and PC-3 (PSCA-negative prostate cancer) xenografts. The mouse was injected with I-124 radiolabeled anti-PSCA diabody (left panel) or shows co-registered microPET/microCT scans of a nude mouse bearing LAPC-9 (PSCA-positive human prostate cancer) and PC-3 (PSCA-negative prostate cancer) xenografts. The mouse was injected with I-124 radiolabeled anti-PSCA minibody (right panel).

FIG. 11 (top panel) provides a schematic representation of the antibody fragments of the invention. FIG. 11 (bottom panel) a shows co-registered microPET/microCT scans of a nude mouse bearing LAPC-9 (PSCA-positive human prostate cancer) and PC-3 (PSCA-negative prostate cancer) xenografts. The mouse was injected with I-124 radiolabeled anti-PSCA diabody.

FIG. 12 shows (top panel) co-registered microPET/microCT scan of a nude mouse bearing LAPC-9 (PSCA-positive human prostate cancer) and PC-3 (PSCA-negative prostate cancer) xenografts. The mouse was injected with I-124 radiolabeled anti-PSCA minibody. The bottom panel is a table showing the 21 hour biodistribution of the minibody and deactivated minibody in different mouse body tissues.

FIG. 13 shows (top panel) co-registered microPET/microCT scans of a nude mouse bearing LAPC-9 (PSCA-positive human prostate cancer) xenograft after injection with I-124 radiolabeled anti-PSCA wild type scFv-Fc antibody. The bottom panel shows co-registered microPET/microCT scans of a nude mouse bearing LAPC-9 (PSCA-positive human prostate cancer) and PC-3 (PSCA-negative prostate cancer) xenografts after injection with I-124 radiolabeled double mutant anti-PSCA scFv-Fc antibody.

DETAILED DESCRIPTION

Figure 2:
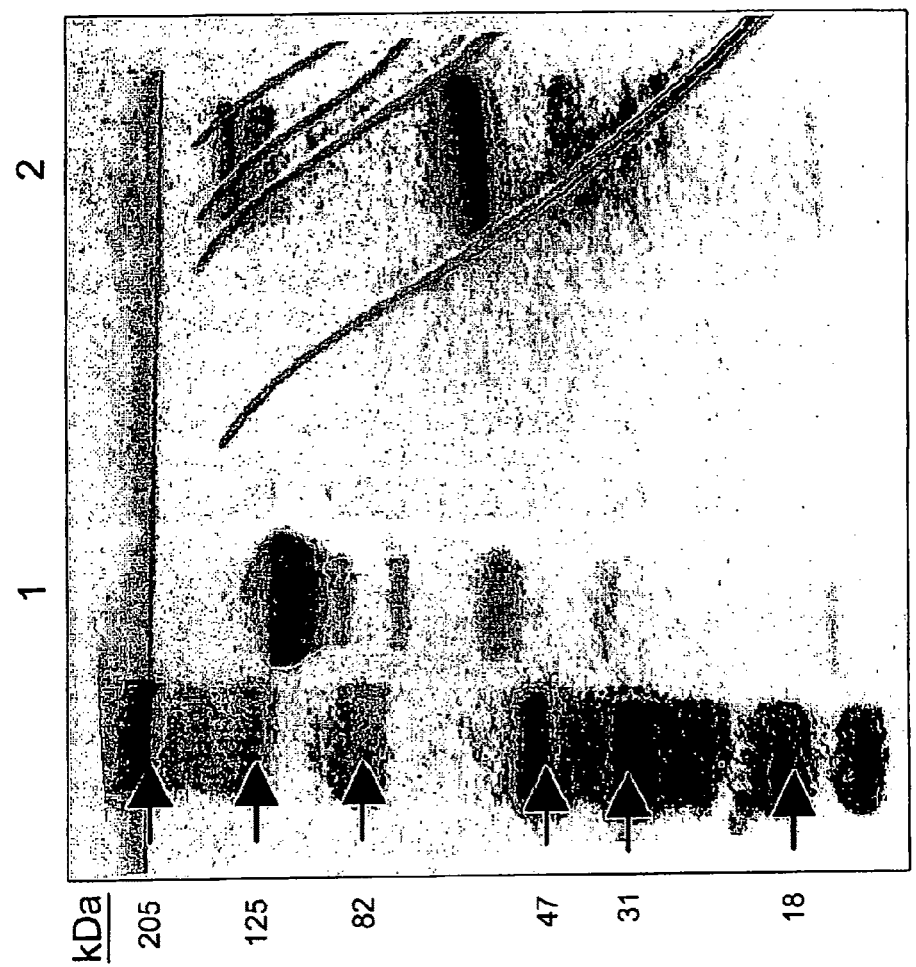
FIG. 2 illustrates SDS-PAGE analysis of anti-PSCA minibody under non-reducing (1) and reducing (2) conditions, showing the 95 kDa covalent dimer and the 47 kDa monomeric subunits.

The present invention provides engineered PSCA-specific humanized antibody fragments, e.g., scFv dimers (diabodies), scFv-CH3 dimers (minibodies), and scFv-Fc, that have in vivo pharmacokinetic and targeting potentials that overcome the shortcomings associated with the use of previously known intact antibodies directed against PSCA for use in the diagnosis, prognosis, and treatment of cancer cells that overexpress cell surface PSCA, such as prostate, bladder, and pancreatic cancer cells.

I. Introduction

PSCA is a novel, glycosylphosphatidylinositol (GPI)-anchored cell surface antigen which is expressed in normal cells, such prostate cells, urothelium, renal collecting ducts, colonic neuroendocrine cells, placenta, normal bladder and urethral transitional epithelial cells. The PSCA gene shows 30% homology to stem cell antigen-2 (SCA-2), a member of the Thy-1/Ly-6 family of glycosylphosphatidylinositol (GPI)-anchored cell surface antigens, and encodes a 123 amino acid protein with an amino-terminal signal sequence, a carboxy-terminal GPI-anchoring sequence, and multiple N-glycosylation sites.

In addition to its expression pattern in normal cells, PSCA is overexpressed by both androgen-dependent and androgen-independent prostate cancer cells, prostate cancer metastases to bone, bladder carcinomas, and pancreatic carcinomas. PSCA is widely overexpressed in all stages of prostate cancer, including high grade prostatic intraepithelial neoplasia (PIN). In situ mRNA analysis localizes PSCA expression to the basal cell epithelium, the putative stem cell compartment of the prostate. Flow cytometric analysis demonstrates that PSCA is expressed predominantly on the cell surface and is anchored by a GPI linkage. Fluorescent in situ hybridization analysis localizes the PSCA gene to chromosome 8q24.2, a region of allelic gain in more than 80% of prostate cancers.

The expression of PSCA observed in cancer, e.g., prostate cancer and bladder cancer, appears to correlate with increasing grade. Furthermore, overexpression of PSCA (i.e., higher expression than found in normal cells) in patients suffering from cancer, e.g., prostate cancer, appears to be indicative of poor prognosis. For example, PSCA is expressed at very high levels in prostate cancer in relation to benign prostatic hyperplasia (BPH). In contrast, the prostate cancer marker PSA is expressed at high levels in both normal prostate and BPH, but at lower levels in prostate cancer, rendering PSA expression useless for distinguishing malignant prostate cancer from BPH or normal glands. Because PSCA expression is essentially the reverse of PSA expression, analysis of PSCA expression can be employed to distinguish prostate cancer from non-malignant conditions.

Accordingly, the expression pattern of PSCA in prostate and other cancers makes it an attractive molecule for various diagnostic and therapeutic strategies. Some intact antibodies against PSCA have been tested for the diagnosis and therapy of prostate cancer. However, the utility of intact anti-PSCA antibodies for the diagnosis or treatment of prostate cancer may be limited by the restricted ability of large sized molecules such as intact antibodies to reach the site of a tumor. As a result, current approaches using intact anti-PSCA antibodies for the diagnosis or treatment of prostate cancer may be limited by the efficacy of antibody delivery.

Furthermore, traditional intact therapeutic monoclonal antibodies must stored at near freezing temperatures to prevent degradation. Additionally, intact antibodies are not suited for oral administration because they are digested quickly in the gut. As such, many patients are administered intact antibodies by way of the less convenient means of injection or infusion in a clinic. As alluded to above, the biodistribution of intact antibodies may be limited, as such large reagents may have difficulty penetrating beyond the periphery of a solid tumor or across the blood-brain barrier, if such distributions are desired.

To overcome the delivery and stability problems associated with the use of intact PSCA antibodies, we have developed a series of engineered PSCA-specific humanized antibody fragments (diabody (scFv dimer, 50 kDa), minibody (scFv-$C_H3$ dimer, 80 kDa), and scFv-Fc, 110 kDa)) that show favorable in vivo pharmacokinetic characteristics and targeting potential.

As a starting point, we began with a murine monoclonal antibody, 1G8, which is specific for PSCA, a cell-surface glycoprotein that is expressed in normal human prostate and bladder. PSCA is overexpressed in prostate cancers (40% of primary tumors and 60-100% of lymph node and bone marrow metastases). It is also highly expressed in transitional carcinomas of the bladder and pancreatic carcinoma. The murine 1G8 anti-PSCA antibody demonstrates substantial anti-tumor activity in vitro and in vivo. In order to develop this antibody for clinical use, 1G8 was humanized by CDR-grafting and subsequent molecular modification of the CDR for optimization, resulting in the 2B3 antibody, a sequence of which is shown in FIG. 1.

We initially found that the humanization process caused a 4-fold reduction in the affinity of the resulting antibody for binding to PSCA. By protein modeling, six framework mutations were specifically chosen to test for a potential increase in binding affinity. As a result of this work, two distinct diabodies were created, parental and affinity matured, both with an eight amino acid linker peptide [(GGGS)$_2$ (SEQ ID NO:3)]. The apparent affinities were determined by Biacore to be $K_D$=5.41 nM and 1.89 nM, respectively. Size exclusion chromatography revealed that homogenous dimers are favored by the parental, but not the affinity matured, diabody. In addition, different linker lengths (5 vs. 8 amino acids) and storage conditions were examined in order to obtain a homogenous dimer preparation. In vitro PSCA binding was demonstrated by immunofluorescence using PSCA-positive prostate cancer cell lines. Diabodies were radioiodinated and retained 17% and 22% immunoreactivity for the parental and affinity matured diabodies, respectively. A microPET study with $^{124}$I-labeled diabody demonstrated effective localization to the PSCA-positive tumor in LAPC-9 xenografted SCID mice. Biodistribution studies with $^{124}$I-labeled diabody showed a tumor uptake of 1.22% ID/g. Through such protein engineering methods, we have optimized parameters such as binding affinity and conformation for the 2B3 diabody.

Further studies were performed to determine the optimal format for in vivo imaging by radioiodinating recombinant fragments with the positron emitter $^{124}$I ($t_{1/2}$=4.2 d) and evaluation with microPET scanning. An intermediately-sized minibody demonstrated excellent tumor uptake of 5.2 (±1.6) percent injected dose per gram (% ID/g) in PSCA-expressing LAPC-9 xenografts (n=12) at 21 h post-injection; rapid clearance from blood and normal tissues resulted in high contrast microPET images (FIG. 12). The positive tumor to control tumor (PC-3) uptake ratio was 2.0, and the tumor-to-carcass ratio was 4.3. The smaller fragment (anti-PSCA diabody) cleared quickly from the circulation and only reached 0.9 (±0.3) % ID/g in LAPC-9 xenografts at 21 h (n=4) (FIG. 11). A larger scFv-Fc fragment, engineered for rapid clearance, attained 3.1 (±0.4) % ID/g in LAPC-9 xenografts compared to PC-3 (1.7±0.2% ID/g) (n=4) (FIG. 13). Accordingly, as described herein, the present invention provides vastly improved in vivo clinical imaging agents for cancers that express PSCA, such as prostate, bladder, and pancreatic cancers, and thus, extends the utility of reagents directed to PSCA beyond the capability of previously described antibodies which have been approved solely for therapy and diagnosis on tissue samples.

II. Definitions

As used herein, the following terms have the meanings ascribed to them unless specified otherwise.

"Prostate stem cell antigen" or "PSCA" refers to nucleic acids (e.g., gene, pre-mRNA, mRNA), polypeptides, polymorphic variants, alleles, mutants, and interspecies homologs that have an amino acid sequence that has greater than about 60% amino acid sequence identity, e.g., about 65%, 70%, 75%, 80%, 85%, 90%, 95%, preferably about 91%, 92%, 93%, 94%, 95%, 96%, 97%, 98%, 99%, or greater amino acid sequence identity, preferably over a region of at least about 25, 50, 100, 200, 500, 1000, or more amino acids, to a polypeptide corresponding to PSCA as described herein. Accession numbers for representative amino acid sequences for PSCA include: CAB97347 (human) and NP_082492 (mouse), among others. Accession numbers for representative nucleic acid sequences for PSCA include: NM_005672 (human) and NM_028216 (mouse), among others.

The term "cancer" refers to human cancers and carcinomas, sarcomas, adenocarcinomas, lymphomas, leukemias, solid and lymphoid cancers, etc. Examples of different types of cancer include, but are not limited to, prostate cancer, renal cancer (i.e., renal cell carcinoma), bladder cancer, lung cancer, breast cancer, thyroid cancer, liver cancer (i.e., hepatocarcinoma), pleural cancer, pancreatic cancer, ovarian cancer, uterine cancer, cervical cancer, testicular cancer, colon cancer, anal cancer, pancreatic cancer, bile duct cancer, gastrointestinal carcinoid tumors, esophageal cancer, gall bladder cancer, rectal cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma. In preferred embodiments, the compositions and methods of the present invention are useful for diagnosing, imaging, proving a prognosis for, and treating prostate, bladder, or pancreatic cancer or subtypes thereof.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of PSCA protein and RNA, as well as local overexpression due to altered protein trafficking patterns and/or augmented functional activity. Overexpression can be detected using conventional techniques for detecting protein (e.g., ELISA, Western blotting, flow cytometry, immunofluorescence, immunohistochemistry, etc.) or mRNA (e.g., RT-PCR, PCR, hybridization, etc.). One skilled in the art will know of other techniques suitable for detecting overexpression of PSCA protein or mRNA. Cancerous cells, e.g., cancerous prostate, bladder, or pancreatic cells, can overexpress PSCA on the cell surface at a level of at least about 5%, 10%, 15%, 20%, 25%, 30%, 35%, 40%, 45%, 50%, 55%, 60%, 65%, 70%, 75%, 80%, 85%, 90%, or 95% in comparison to corresponding normal, non-cancerous cells. Cancerous cells can also have at least about a 1-fold, 2-fold, 3-fold, 4-fold, 5-fold, 6-fold, or 7-fold higher level of PSCA transcription or translation in comparison to normal, non-cancerous cells. In certain instances, the cancer cell sample is autologous. In some cells, PSCA expression is very low or undetectable. As such, expression includes no expression, i.e., expression that is undetectable or insignificant.

The term "biological sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., prostate, kidney, bladder, lymph node, liver, bone marrow, blood cell, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

The terms "cancer-associated antigen," "tumor-specific marker," or "tumor marker" interchangeably refers to a molecule (typically protein, carbohydrate, or lipid) that is preferentially expressed in a cancer cell in comparison to a normal cell, and which is useful for the preferential targeting of a pharmacological agent to the cancer cell. A marker or antigen can be expressed on the cell surface or intracellularly. Oftentimes, a cancer-associated antigen is a molecule that is overexpressed or stabilized with minimal degradation in a cancer cell in comparison to a normal cell, for instance, 1-fold over expression, 2-fold overexpression, 3-fold overexpression, or more in comparison to a normal cell. Oftentimes, a cancer-associated antigen is a molecule that is inappropriately synthesized in the cancer cell, for instance, a molecule that contains deletions, additions, or mutations in comparison to the molecule expressed on a normal cell. Oftentimes, a cancer-associated antigen will be expressed exclusively in a cancer cell and not synthesized or expressed in a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian, and colorectal. Exemplified intracellular tumor markers include, for example, mutated tumor suppressor or cell cycle proteins, including p53. The PSCA antigen of the present invention serves as a tumor cell marker for prostate, bladder, and pancreatic cancer.

A "label," "detectable moiety," or "imaging agent" is a composition detectable by spectroscopic, photochemical, biochemical, immunochemical, chemical, or other physical means. A detectable moiety can be coupled either directly or indirectly to the PSMA polypeptide or peptide fragment described herein using methods well known in the art. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, electron-dense reagents, biotin, digoxigenin, haptens, and the like.

The term "radionuclide" refers to a nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Radionuclides suitable for use in the present invention include, but are not limited to, fluorine 18 ($^{18}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$), silver 111 ($^{111}Ag$), indium 111 ($^{111}In$), iodine 124 ($^{124}I$), iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 ($^{166}Ho$), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth 212 ($^{212}Bi$). As used herein, the "m" in $^{117m}Sn$ and $^{99m}Tc$ stands for meta state. Additionally, naturally-occurring radioactive elements such as uranium, radium, and thorium, which typically represent mixtures of radioisotopes, are suitable examples of radionuclides.

As described herein, compositions comprising a radionuclide coupled to an antibody or antibody fragment that recognizes PSCA are particularly useful for therapeutic, imaging, diagnostic, or prognostic purposes in a subject. The radionuclide can be directly coupled to the PSCA-specific antibody or fragment, directly coupled to a linking group (e.g., a peptide linking group), or bound to a chelating agent. Methods for coupling radionuclides to proteins or linking groups or binding radionuclides to chelating agents are known to one of skill in the art. In certain instances, the compositions of the present invention comprise PSCA-specific antibodies and antibody fragments conjugated to a bifunctional chelating agent that contains a radionuclide such as $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, and/or $^{212}Bi$ bound thereto. Alternatively, compositions of the present invention comprise PSCA-specific antibody or fragments or linking groups conjugated thereto that are radiolabeled with a radionuclide such as $^{18}F$, $^{124}I$, $^{125}I$, and/or $^{131}I$. In certain other instances, the imaging compositions of the present invention comprise PSCA-specific antibody or fragments conjugated to a bifunctional chelating agent that contains a radionuclide such as $^{55}Co$, $^{60}Cu$, $^{61}Cu$, $^{62}Cu$, $^{64}Cu$, $^{66}Ga$, $^{67}Cu$, $^{67}Ga$, $^{68}Ga$, $^{82}Rb$, $^{86}Y$, $^{87}Y$, $^{90}Y$, $^{111}In$, $^{99m}Tc$, and/or $^{201}Tl$ bound thereto. Alternatively, the imaging compositions of the present invention comprise PSCA antibody fragments or linking groups conjugated thereto that are radiolabeled with a radionuclide such as $^{18}F$ and/or $^{131}I$. Further, $Gd^{+3}$ may be conjugated to the antibody fragments of the invention for use as a contrast reagent in applications such as MRI.

A "chelating agent" refers to a compound which binds to a metal ion, such as a radionuclide, with considerable affinity and stability. In addition, the chelating agents of the present invention are bifunctional, having a metal ion chelating group at one end and a reactive functional group capable of binding to peptides, polypeptides, or proteins at the other end. Methods for conjugating bifunctional chelating agents to peptides, polypeptides, or proteins are well known in the art. Suitable bifunctional chelating agents include, but are not limited to, 1,4,7,10-tetraazacyclododecane-N,N',N'',N'''-tetraacetic acid (DOTA), a bromoacetamidobenzyl derivative of DOTA (BAD), 1,4,8,11-tetraazacyclotetradecane-N,N',N'',N'''-tetraacetic acid (TETA), diethylenetriaminepentaacetic acid (DTPA), the dicyclic dianhydride of diethylenetriaminepentaacetic acid (ca-DTPA), 2-(p-isothiocyanatobenzyl)diethylenetriaminepentaacetic acid (SCNBzDTPA), and 2-(p-isothiocyanatobenzyl)-5(6)-methyl-diethylenetriaminepentaacetic acid (MxDTPA) (see, e.g., Ruegg et al., *Cancer Res.*, 50:4221-4226 (1990); DeNardo et al., *Clin. Cancer Res.*, 4:2483-2490 (1998)). Other chelating agents include EDTA, NTA, HDTA and their phosphonate analogs such as EDTP, HDTP, and NTP (see, e.g., Pitt et al., INORGANIC CHEMISTRY IN BIOLOGY AND MEDICINE, Martell, Ed., American Chemical Society, Washington, D.C., 1980, pp. 279-312; Lindoy, THE CHEMISTRY OF MACROCYCLIC LIGAND COMPLEXES, Cambridge University Press, Cambridge, 1989; Dugas, BIOORGANIC CHEMISTRY, Springer-Verlag, New York, 1989).

The term "nanoparticle" refers to a microscopic particle whose size is measured in nanometers, e.g., a particle with at least one dimension less than about 100 nm. Nanoparticles are particularly useful as detectable moieties because they are small enough to scatter visible light rather than absorb it. For example, gold nanoparticles possess significant visible light extinction properties and appear deep red to black in solution. As a result, compositions comprising PSCA-specific antibody or fragments conjugated to nanoparticles can be used for the in vivo imaging of tumors or cancerous cells in a subject. Methods for attaching polypeptides or peptides nanoparticles are well known in the art and are described in, e.g., Liu et al., Biomacromolecules, 2:362-368 (2001); Tomlinson et al., *Methods Mol. Biol.*, 303:51-60 (2005); and Tkachenko et al., *Methods Mol. Biol.*, 303:85-99 (2005). At the small end of the size range, nanoparticles are often referred to as clusters. Metal, dielectric, and semiconductor nanoparticles have been formed, as well as hybrid structures (e.g. core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to a PSCA-specific antibody or fragment of the present invention, can be used as imaging agents for the in vivo detection of tumor tissue such as prostate, bladder, or pancreatic cancer tissue. Alternatively, nanoparticles can be used in therapeutic applications as drug carriers that, when conjugated to a PSCA-specific antibody or fragment of the present invention, deliver chemotherapeutic agents, hormonal therapeutic agents, radiotherapeutic agents, toxins, or any other cytotoxic or anti-cancer agent known in the art to cancerous cells that overexpress PSCA on the cell surface.

The term "recombinant," when used with reference, e.g., to a cell, nucleic acid, protein, or vector, indicates that the cell, nucleic acid, protein, or vector has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "therapeutically effective amount or dose" or "therapeutically sufficient amount or dose" herein is meant a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins) and as further described herein.

III. Antibodies and Fragments

The term "antibody" refers generally to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability produced by any means known in the art, such as by protease treatment or recombinantly (e.g., Fab', F(ab')$_2$, Fab, Fv and rIgG. See, also, Pierce Catalog and Handbook, 1994-1995 (Pierce Chemical Co., Rockford, Ill.). See, also, e.g., Kuby, J., *Immunology*, 3.sup.rd Ed., W. H. Freeman & Co., New York (1998). The term also refers to recombinant single chain Fv fragments (scFv). The term antibody also includes bivalent or bispecific molecules, diabodies, triabodies, and tetrabodies, minibodies, and scFv-Fc structures. See, e.g., Weiner et al. (2000) *Oncogene* 19: 6144; Quiocho (1993) *Nature* 362:293. Bivalent and bispecific molecules are described in, e.g., Kostelny et al. (1992) *J Immunol.* 148: 1547; Pack and Pluckthun (1992) *Biochemistry*, 31:1579; Hollinger et al., 1993, supra; Gruber et al. (1994) *J. Immunol:* 5368; Zhu et al. (1997) *Protein Sci* 6:781; Hu et al. (1996) *Cancer Res.* 56:3055; Adams et al. (1993) *Cancer Res.* 53:4026; and McCartney, et al. (1995) *Protein Eng.* 8:301.

The term "antibody fragment" refers generally to any portion of an antibody that has antigen binding capability. The term includes structures that naturally occur in nature such as Fab and Fc fragments that result from protease treatment of intact antibodies or to engineered non-naturally occurring antibody structures that result from molecular biological or other manipulations that join antibody domains in configurations not normally found in nature. For example, non-native configurations of antibody domains can be derived through a variety of methods known in the art such as by construction of fusion proteins, with or without linkers, such as peptide sequences, or by covalent linkage with chemical linkers.

The term "specifically binds" means that an antibody or antibody fragment predominantly binds to a particular antigen or epitope, such as PSCA.

The term "Fc" refers generally a portion of an antibody structure composed of two heavy chains that each contribute two to three constant domains, depending on the class of the antibody. It will be appreciated by the skilled artisan that an Fc can be generated by any method known in the art, such as proteolysis or by recombinant expression methods.

An antibody immunologically reactive with a particular antigen may be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" refer to the variable region of an immunoglobulin heavy chain of an antibody, including the heavy chain of an Fv, scFv, or Fab. References to "$V_L$" refer to the variable region of an immunoglobulin light chain, including the light chain of an Fv, scFv, dsFv or Fab.

Figure 7A:
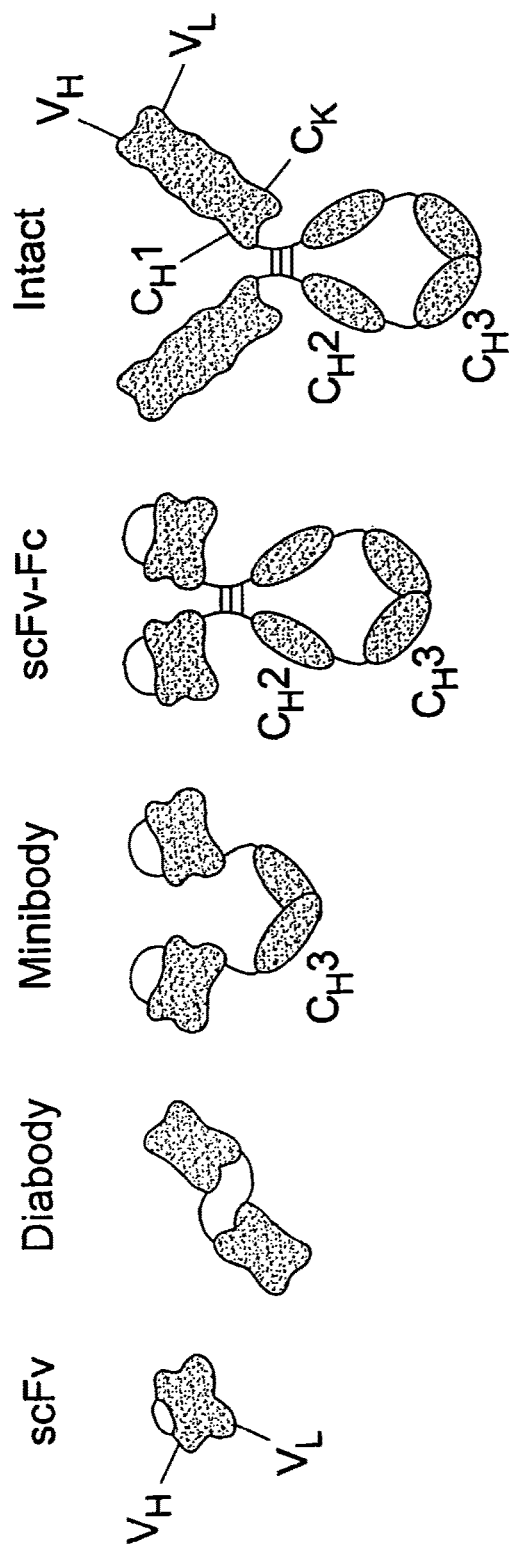
FIG. 7(a) provides a schematic representation of the antibody fragments of the invention.
Figure 7B:
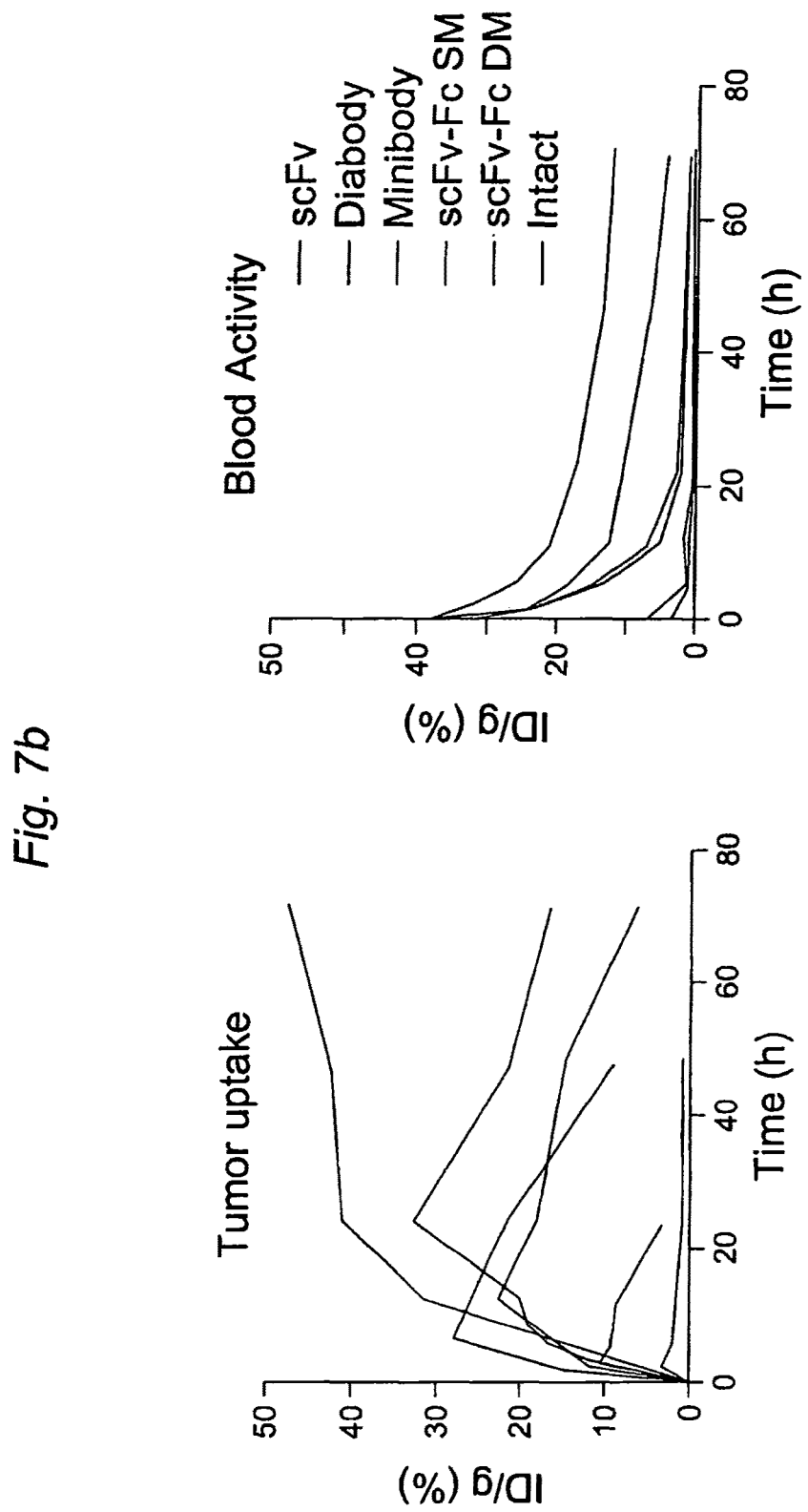
FIG. 7(b) shows the comparative tumor uptake and blood activity of the antibody fragments of (a) over time.

The phrase "single chain Fv" or "scFv" refers to an antibody fragment in which the variable domains of the heavy chain and of the light chain of a traditional two chain antibody have been joined to form one chain. Typically, a linker peptide is inserted between the two chains to allow for proper folding and creation of an active binding site. Thus, the linker serves to join a $V_L$ domain to a $V_H$ domain as shown, for instance, in FIG. 7(*a*).

The terms "scFv dimer" and "diabody" refer generally to an antibody fragment comprising a dimer formed by the interaction between two single chain Fv monomers as described above and as illustrated, for example, in FIG. 7(*a*).

The terms "scFv-CH3 dimer" or "minibody" refer generally to an antibody fragment comprising a dimer formed by the joining of monomers comprising the structure of a scFv joined to a constant region heavy chain, such as the CH3 domain. Generally, a linker is used to join the scFv, via the VH chain, to the CH3 domain. Such linkers may advantageously contain one or more cysteine residues to allow disulfide bonding of the scFv-CH3 monomers to form a scFv-CH3 dimer or minibody as illustrated, for example, in FIG. 7(a).

The term "scFv-Fc" refers generally to an antibody fragment comprising a dimer formed by the joining of monomers comprising the structure of a scFv joined to an antibody Fc domain. Generally, a linker is used to join the scFv, via the VH chain, to the Fc domain. Such linkers may advantageously contain one or more cysteine residues to allow disulfide bonding to provide a scFv-Fc as illustrated, for example, in FIG. 2.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, and the like; or (b) the variable region, or a portion thereof, is altered, replaced or exchanged with a variable region having a different or altered antigen specificity.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., *Nature* 321:522-525 (1986); Riechmann et al., *Nature* 332: 323-329 (1988); and Presta, *Curr. Op. Struct. Biol.* 2:593-596 (1992)). Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

"Epitope" or "antigenic determinant" refers to a site on an antigen to which an antibody binds. It will be understood that an epitope can be either a protein, carbohydrate, lipid, nucleic acid, or small molecule entity, although protein epitopes are the most common. In the case of proteins, epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed (1996).

Methods of preparing polyclonal antibodies are known to the skilled artisan (e.g., Coligan, supra; and Harlow & Lane, supra). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler & Milstein, *Nature* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, pp. 59-103 (1986)). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Human antibodies can be produced using various techniques known in the art, including phage display libraries (Hoogenboom & Winter, *J. Mol. Biol.* 227:381 (1991); Marks et al., *J. Mol. Biol.* 222:581 (1991)). The techniques of Cole et al. and Boemer et al. are also available for the preparation of human monoclonal antibodies (Cole et al., Monoclonal Antibodies and Cancer Therapy, p. 77 (1985) and Boemer et al., *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *BioTechnology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg & Huszar, *Inter. Rev. Immunol.* 13:65-93 (1995).

In some embodiments, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston et al., *Proc. Nat'l Acad. Sci. USA* 8:5879 (1988); Bird et al., *Science* 242:4236 (1988); Glockshuber et al., *Biochemistry* 29:1362 (1990); U.S. Pat. No. 4,946,778, U.S. Pat. No. 5,132,405 and Stemmer et al., *Biotechniques* 14:256-265 (1993). Generally the peptide linker will have no specific biological activity other than to join the regions or to preserve some minimum distance or other spatial relationship between the $V_H$ and $V_L$. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser (SEQ ID NO:5) (GGGS; SEQ ID NO:4), preferably 2, 3, 4, 5, or 6 such sequences. However, it is to be appreciated that some amino acid substitutions within the linker can be made. For example, a valine can be substituted for a glycine.

Methods of making scFv antibodies have been described. See, Huse et al., supra; Ward et al. supra; and Vaughan et al., supra. In brief, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell. The scFv that specifically bind to the desired antigen are typically found by panning of a phage display library. Panning can be performed by any of several methods. Panning can conveniently be performed using cells expressing the desired antigen on their surface or using a solid surface coated with the desired antigen. Conveniently, the surface can be a magnetic bead. The unbound phage are washed off the solid surface and the bound phage are eluted.

The antibodies used in the practice of this invention may include bispecific antibodies. Bispecific antibodies are monoclonal, preferably human or humanized, antibodies that have binding specificities for at least two different antigens or that have binding specificities for two epitopes on the same antigen.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature* 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.* 10:3655-3659 (1991). Antibody variable domains with the desired binding specificities (antibody-antigen combining sites) can be fused to immunoglobulin constant domain sequences. The fusion preferably is with an immunoglobulin 5 heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology* 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

IV. Diagnostic and Prognostic Methods

In certain aspects, the present invention provides methods of diagnosing or providing a prognosis for cancer, e.g., a cancer that overexpresses PSCA, such as prostate, bladder, or pancreatic cancer. As used herein, the term "providing a prognosis" refers to providing a prediction of the probable course and outcome of a cancer or the likelihood of recovery from the cancer. In certain instances, cancer patients with negative or low PSCA expression have a longer disease-specific survival as compared to those with high PSCA expression. As such, the level of PSCA expression can be used as a prognostic indicator, with negative or low expression as an indication of a good prognosis, e.g., a longer disease-specific survival.

The methods of the present invention can also be useful for diagnosing the severity of a cancer, e.g., a cancer that overexpresses PSCA. As a non-limiting example, the level of PSCA expression can be used to determine the stage or grade of a cancer such as prostate cancer, e.g., according to the Tumor/Nodes/Metastases (TNM) system of classification (International Union Against Cancer, 6th edition, 2002) or the Whitmore-Jewett staging system (American Urological Association). Typically, cancers are staged using a combination of physical examination, blood tests, and medical imaging. If tumor tissue is obtained via biopsy or surgery, examination of the tissue under a microscope can also provide pathologic staging. In certain instances, cancer patients with high PSCA expression have a more severe stage or grade of that type of cancer. As such, the level of PSCA expression can be used as a diagnostic indicator of the severity of a cancer or of the risk of developing a more severe stage or grade of the cancer. In certain other instances, the stage or grade of a cancer assists a practitioner in determining the prognosis for the cancer and in selecting the appropriate cancer therapy.

The diagnostic and prognostic methods of the present invention advantageously utilize novel engineered humanized antibody fragments that bind to cell surface PSCA. Such antibody fragments can be used to determine a level of PSCA expression in tumor tissue or cancerous cells and then compared to a baseline value or range. Typically, the baseline value is representative of PSCA expression levels in a healthy person not suffering from cancer. Variation of PSCA levels from the baseline range (i.e., either up or down) indicates that the subject has a cancer or is at risk of developing a cancer. In some embodiments, the level of PSCA expression is measured by taking a blood, urine, prostatic fluid, or tumor tissue sample from a subject and measuring the amount of PSCA in the sample using any number of detection methods known in the art. For example, a pull-down assay can be performed on samples such as serum or prostatic fluid using the PSCA antibody fragments described herein coupled to magnetic beads (e.g., Dynabeads®; Invitrogen Corp., Carlsbad, Calif.) to determine the level of PSMA expression.

In some embodiments, the expression of PSCA in a cancerous or potentially cancerous tissue may be evaluated by visualizing the presence and/or localization of PSCA in the subject. Any technique known in the art for visualizing tumors, tissues, or organs in live subjects can be used in the imaging methods of the present invention. Preferably, the in vivo imaging of cancerous or potentially cancerous tissue is performed using an antibody fragment that binds to the surface of cells expressing PSCA, wherein the PSCA antibody fragment is linked to an imaging agent such as a detectable moiety (i.e., a contrast agent). A detectable moiety can be coupled either directly or indirectly to the PSCA antibody fragment described herein using methods well known in the art. A wide variety of detectable moieties can be used, with the choice of label depending on the sensitivity required, ease of conjugation with the PSCA antibody fragments, stability requirements, and available instrumentation and disposal provisions. Suitable detectable moieties include, but are not limited to, radionuclides as described above, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

The detectable moiety can be visualized in a subject using any device or method known in the art. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a detectable moiety linked to a PSCA antibody fragment of the present invention. Positron Emission Tomography (PET) is another suitable technique for detecting radiation in a subject to visualize tumors in living patients according to the methods of the present invention. Furthermore, U.S. Pat. No. 5,429,133 describes a laparoscopic probe for detecting radiation concentrated in solid tissue tumors. Miniature and flexible radiation detectors intended for medical use are produced by Intra-Medical LLC, Santa Monica, Calif. Magnetic Resonance Imaging (MRI) or any other imaging technique known to one of skill in the art (e.g., radiography (i.e., X-rays), computed tomography (CT), fluoroscopy, etc.) is also suitable for detecting the radioactive emissions of radionuclides.

Various in vivo optical imaging techniques that are suitable for the visualization of fluorescent and/or enzymatic labels or markers include, but are not limited to, fluorescence microendoscopy (see, e.g., Flusberg et al., *Optics Lett.*, 30:2272-2274 (2005)), fiber-optic fluorescence imaging (see, e.g., Flusberg et al., *Nature Methods*, 2:941-950 (2005)), fluorescence imaging using a flying-spot scanner (see, e.g., Ramanujam et al., *IEEE Trans. Biomed. Eng.*, 48:1034-1041 (2001)), catheter-based imaging systems (see, e.g., Funovics et al., *Radiology*, 231:659-666 (2004)), near-infrared imaging systems (see, e.g., Mahmood et al., *Radiology*, 213:866-870 (1999)), fluorescence molecular tomography (see, e.g., Gurfinkel et al., *Dis. Markers*, 19:107-121 (2004)), and bioluminescent imaging (see, e.g., Dikmen et al., *Turk. J. Med. Sci.*, 35:65-70 (2005)).

The PSCA antibody fragments of the present invention, when conjugated to any of the above-described detectable moieties, can be administered in doses effective to achieve the desired image of tumor tissue or cancerous cells in a subject. Such doses may vary widely, depending upon the particular detectable label employed, the type of tumor tissue or cancerous cells subjected to the imaging procedure, the imaging equipment being used, and the like. However, regardless of the detectable moiety or imaging technique used, such detection is aimed at determining where the PSCA antibody fragment is concentrated in a subject, with such concentration being an indicator of the location of a tumor or tumor cells. Alternatively, such detection is aimed at determining the extent of tumor regression in a subject, with the size of the tumor being an indicator of the efficacy of cancer therapy. For example, evidence exists that PSCA expression can serve as a surrogate marker for other changes in cancer, such as PTEN deletion or androgen receptor activation; thus, the PSCA-specific antibody fragments of the present invention may be used to monitor a patient's response to treatments that target these pathways.

V. Methods of Administration and Diagnostic and Pharmaceutical Compositions

As described herein, antibody fragments that bind to PSCA on the surface of cells such as cancer cells are particularly useful in treating, imaging, diagnosing, and/or providing a prognosis for cancers such as prostate, bladder, and pancreatic cancer. For therapeutic applications, the PSCA antibody fragments of the present invention can be administered alone or co-administered in combination with conventional chemotherapy, radiotherapy, hormonal therapy, and/or immunotherapy.

As a non-limiting example, PSCA antibody fragments can be co-administered with conventional chemotherapeutic agents including alkylating agents (e.g., cisplatin, cyclophosphamide, carboplatin, ifosfamide, chlorambucil, busulfan, thiotepa, nitrosoureas, etc.), anti-metabolites (e.g., 5-fluorouracil, azathioprine, methotrexate, fludarabine, etc.), plant alkaloids (e.g., vincristine, vinblastine, vinorelbine, vindesine, podophyllotoxin, paclitaxel, docetaxel, etc.), topoisomerase inhibitors (e.g., amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, plicamycin, etc.), and the like.

PSCA antibody fragments can also be co-administered with conventional hormonal therapaeutic agents including, but not limited to, steroids (e.g., dexamethasone), finasteride, aromatase inhibitors, tamoxifen, and gonadotropin-releasing hormone agonists (GnRH) such as goserelin.

Additionally, PSCA antibody fragments can be co-administered with conventional immunotherapeutic agents including, but not limited to, immunostimulants (e.g. *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, PSCA antibody fragments can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In some embodiments, the compositions of the present invention comprise PSCA antibody fragments and a physiologically (i.e., pharmaceutically) acceptable carrier. As used herein, the term "carrier" refers to a typically inert substance used as a diluent or vehicle for a drug such as a therapeutic agent. The term also encompasses a typically inert substance that imparts cohesive qualities to the composition. Typically, the physiologically acceptable carriers are present in liquid, solid, or semi-solid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Examples of solid or semi-solid carriers include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. Since physiologically acceptable carriers are determined in part by the particular composition being administered as well as by the particular method used to administer the composition, there are a wide variety of suitable formulations of pharmaceutical compositions of the present invention (see, e.g., *Remington's Pharmaceutical Sciences*, 17$^{th}$ ed., 1989).

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged PSCA antibody fragment suspended in diluents, e.g., water, saline, or PEG 400; (b) capsules, sachets, or tablets, each containing a predetermined amount of a PSCA antibody fragment, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a PSCA antibody fragment in a flavor, e.g., sucrose, as well as pastilles comprising the polypeptide or peptide fragment in an inert base, such as gelatin and glycerin or sucrose and acacia emulsions, gels, and the like, containing, in addition to the polypeptide or peptide, carriers known in the art.

The PSCA antibody fragment of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged PSCA antibody fragment with a suppository base. Suitable suppository bases include natural or synthetic triglycerides or paraffin hydrocarbons. In addition, it is also possible to use gelatin rectal capsules which contain a combination of the PSCA antibody fragment of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a PSCA antibody fragment. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of cancer, the PSCA antibody fragments utilized in the pharmaceutical compositions of the present invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the PSCA antibody fragment being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular PSCA antibody fragment in a particular patient. Determination of the proper dosage for a particular situation is within the skill of the practitioner. Generally, treatment is initiated with smaller dosages which are less than the optimum dose of the PSCA antibody fragment. Thereafter, the dosage is increased by small increments until the optimum effect under circumstances is reached. For convenience, the total daily dosage may be divided and administered in portions during the day, if desired.

VI. Kits

The present invention also provides kits for carrying out the therapeutic, diagnostic, prognostic, and imaging assays described herein. The kits will typically be comprised of one or more containers containing PSCA antibody fragments that bind to cell surface PSCA, e.g., in dehydrated form, with instructions for their rehydration and administration. For example, one container of a kit may hold the dehydrated PSCA antibody fragments and another container may hold a buffer suitable for rehydrating the dry components. Kits can include any of the compositions noted above, and optionally further include additional components such as instructions to practice the desired method, control antibodies, antigens, polypeptides or peptides such as a negative control antibody or a positive control antigen, a robotic armature for mixing kit components, and the like.

EXAMPLES

The following examples are offered to illustrate, but not to limit the claimed invention.

Example 1

Design and Gene Assembly of Anti-PSCA Antibody Fragments

The 2B3 variable light ($V_L$) and variable heavy ($V_H$) genes were derived from the humanized version of the mouse monoclonal 1G8 antibody. CDR grafting had been previously used to construct the intact humanized antibody (Z. Gu, T. Olafsen et al., 2005). Starting from the DNA of the intact 2B3 antibody in the pEE12 expression vector, primers were designed to amplify the individual $V_L$- and $V_H$ chains. The $V_L$ chain contained a AgeI restriction site while the $V_H$ chain included a XhoI restriction site at its C-terminal end. The two genes were then fused by overlap-extension PCR to produce the single chain Fv (scFv) fragments with the orientation of $V_L$-$V_H$, joined by an 18 residue long linker, which is GlySer rich. Following overlap PCR, the product was cloned into TOPO vector (Stratagene) and sequenced. Subcloning continued into pUC18 with the restriction sites AgeI and EcoRI where the to fuse a signal peptide to the 5'-end (upstream) of the $V_L$ gene and the $V_H$ gene was fused to the human IgG1 $C_H3$ domain via the human IgG1 hinge including a 10 residue GlySer peptide linker. The final sequence of the construct is shown in FIG. 1. Finally, the minibody was cloned into the pEE12 (Lonna Biologics, Slough, UK) mammalian expression vector using the restriction sites XbaI and EcoRI. This vector contains the hCMV promoter and the glutamine synthetase gene for selection (Bebbington et al., 1992).

Example 2

Expression, Selection and Purification of Minibodies

A total of $2\times10^6$ NS0 mouse myeloma cells (Galfre and Milstein, 1981) were transfected with 10 ug of linearized (cut with SalI) vector DNA by electroporation and selected in glutamine-deficient media as described (Yazaki, Shively et al. 2001; Yazaki, Sherman et al. 2004). Minibody clones were screened for expression by ELISA, whereby the desired protein was captured by goat anti-human IgG (Fc specific) and detected by alkaline phosphastase (AP)-conjugated goat anti-human IgG (Fc specific) (both from Jackson ImmunoResearch Labs, West Grove, Pa.). The highest producing clones were expanded and brought to terminal culture.

Minibodies were purified by first treating the cell culture supernatant with 5% AG1®-X8, 100-200 mesh (Bio-Rad laboratories, Hercules, Calif.) overnight to remove phenol red and cell debris, then concentrated down to 100 ml and dialyzed versus 50 mM Acetic Acid, pH 5.0. Protein was then loaded onto a 1.6 ml cation exchange chromatography column (Poros®). Proteins were eluted with a NaCl gradient from 0-0.25M in the presence of 50 mM acetic acid, pH 5.0. Combined eluted fractions (18 ml), containing desired minibody was diluted up to 100 ml with 50 mM MES, pH 6.5 and reloaded onto the cation exchange column. Proteins were eluted with a NaCl gradient from 0-0.3 M in the presence of MES, pH 6.5. Minibody was then dialysed against PBS using a molecular porous membrane tubing (mwco: 30,000) and concentrated with a Vivascience Vivaspin 20 (mwco: 30,000).

Example 3

Characterization of Antibody Fragments

Size and composition of purified proteins was analyzed by SDS-PAGE (FIG. 2) under non-reducing and reducing (1 mM DTT) conditions. Native structural size was determined by size exclusion columns (Superdex 75) (Pharmacia) (FIG. 3).

To examine the structural characteristics of the 2B3 minibody, SDS-PAGE was conducted under reducing and non-reducing conditions. The minibody migrated with a MW of ~47 kDa under reducing conditions and ~95 kDa under non-reducing (FIG. 2). Binding activity by flow cytometry and immunofluoresecent staining (FIGS. 4 and 5) in two distinct cell types demonstrated the minibody recognizes cellular PSCA. The minibody's apparent affinity with respect to its intact antibody counterpart and the original mouse monoclonal antibody (1G8), was determined by competition ELISA. The relative affinity of 1G8 was measured to be 5 nM, the humanized 2B3 antibody was 25 nM, whereas the minibody was 46 nM. Thus the single-chain protein folding format of the minibody has caused it to be 9.2 fold lower in its relative affinity than the murine antibody and relatively ~2 fold lower in affinity than the intact 2B3 antibody.

PSCA relative binding affinity for the minibodies was determined by competition ELISA in which microtiter plate wells were coated with purified PSCA-Fc (Z Gu, T. Olafsen et al. 2006).

Flow Cytometry was conducted to assess cellular PSCA binding activity (FIG. 4). An EBV transfected B-cell lymphoma cell line expressing exogenous PSCA and a PSCA transfected LN-CaP stable cell line were used. Briefly, cells 5×10⁵ were incubated for 30 min on ice with 100 μl of minibody at 2 ug/ml concentration. Cells were washed and stained with goat anti-hFc Alexa 488 conjugated antibody at 1:500 dilution.

Figure 5:
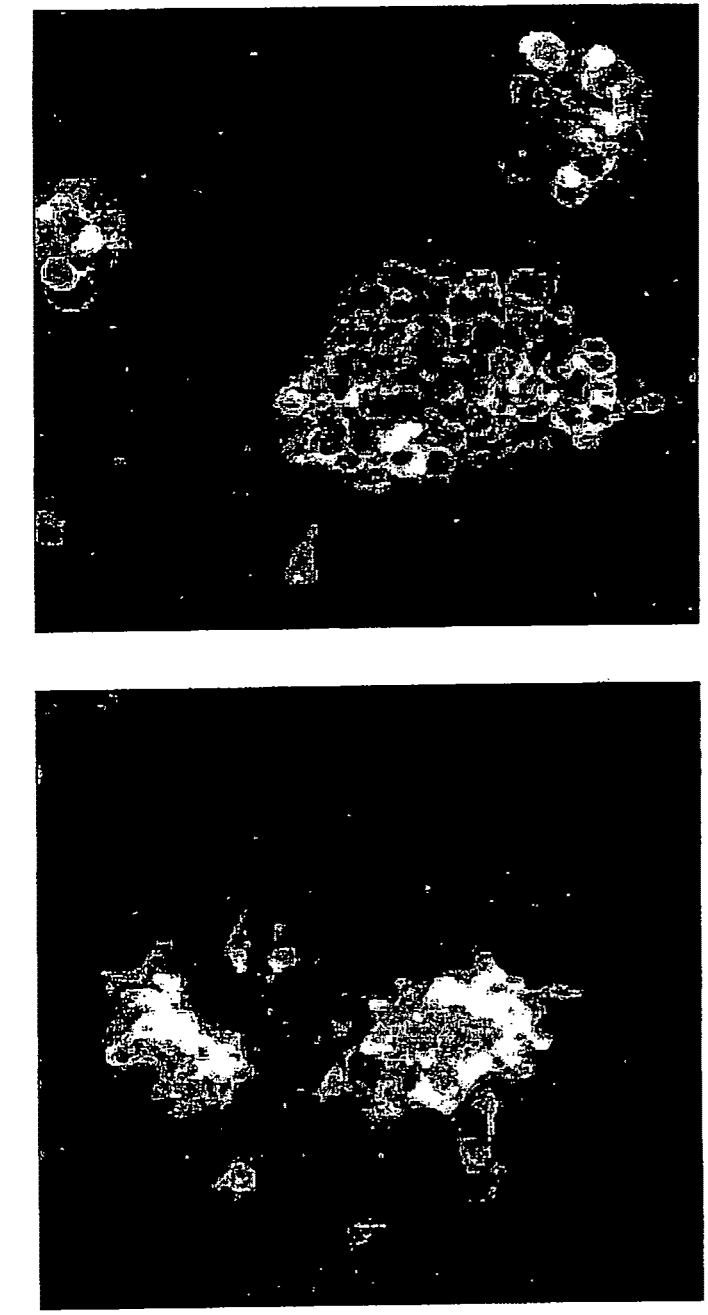
FIG. 5 illustrates the binding of anti-PSCA minibody to antigen-positive cells by immnunofluorescence microscopy.

For immunofluorescence studies, LNCaP cells were grown on glass coverslips coated with poly-L-lysine. Cells were treated in a non-permeabilized fashion as described in (Z Gu 2000). Minibody at 2 mg/ml in PBS/1% BSA was added for 60 min and washed twice with PBS/1% BSA. Alexa488 conjugated goat anti-human IgG (1:500 dilution) (Molecular Probes, Eugene Oreg.) was added for 30 min and washed three times with PBS. Slides were mounted in vectashield (Vector Laboratory, Inc., Burlingame, Calif., USA) and imaged using a Axioskop 2 fluorescent microscope (Zeiss) (FIG. 5).

For radioiodination and microPET imaging, purified minibody was radioiodinated with the positron emitting isotope $^{124}$I (sodium iodide in 0.02 M NaOH; radionuclide purity >99%) provided by V. G. Khlopin Radium Institute & RITVERC GmbH (St. Petersburg, Russia) as previously described (Kenanova, Olafsen et al. 2005). Immunoreactivity was assayed by incubating radioiodinated-minibody with an excess amount of SKW-PSCA+ cells for an hour and spinning down the cells for counting.

Example 4 microPET Imaging of Xenografts Using 124-I anti-PSCA Diabody

Figure 6:
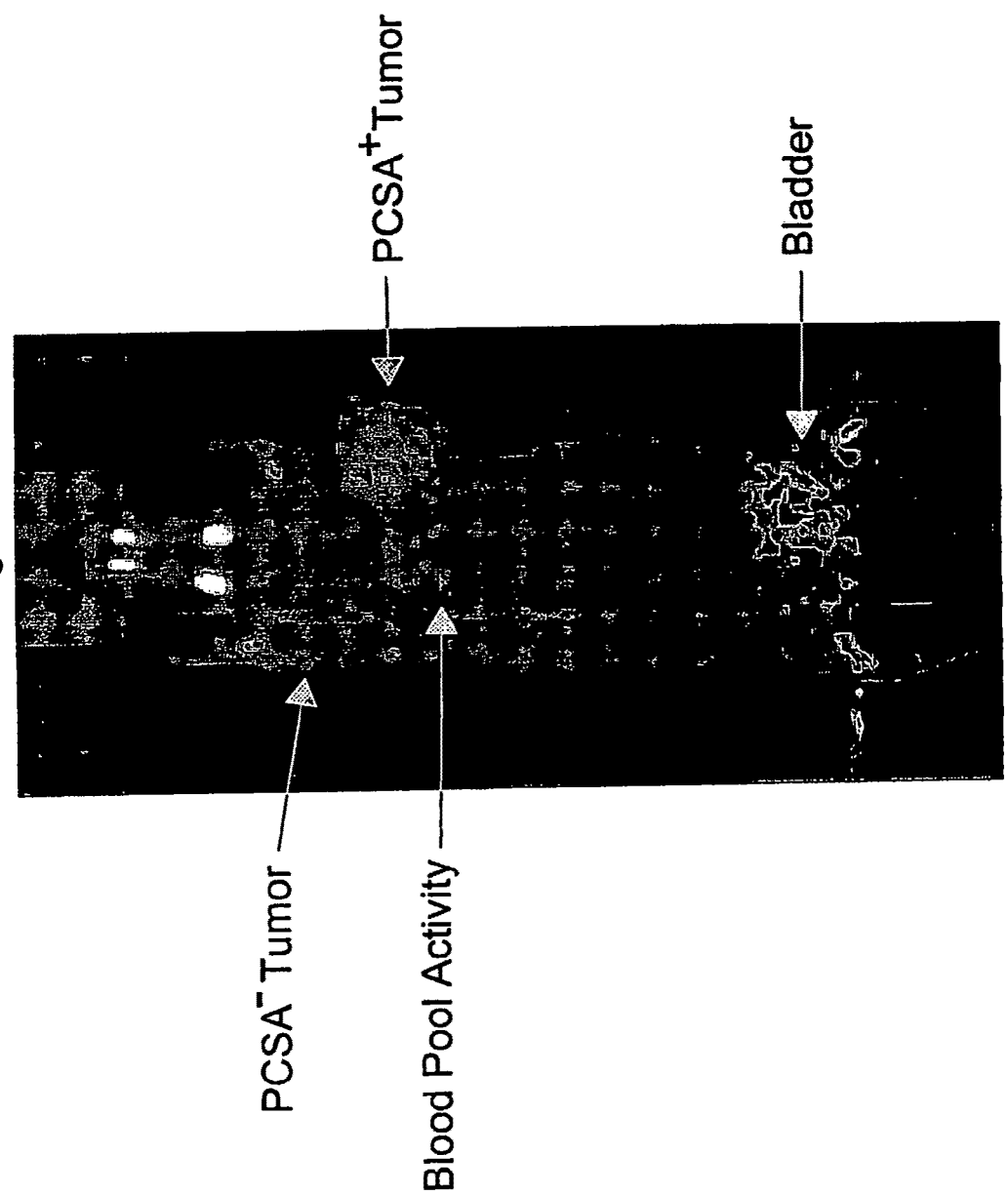
FIG. 6 shows co-registered microPET/microCT scans of a nude mouse bearing LAPC-9 (PSCA-positive human prostate cancer) and PC-3 (PSCA-negative prostate cancer) xenografts. The mouse was injected with I-124 radiolabeled anti-PSCA.

To evaluate tumor targeting of the $^{124}$I-minibody, antigen positive (LAPC-9 prostate carcinoma) or antigen-negative (PC-3 prostate carcinoma) xenografts were established by subcutaneous inoculation in 8 SCID mice. MicroPET imaging studies were conducted on animals bearing PSCA-positive tumors averaging 488 mg (range, 64-1236 mg) and 574 mg. Mice were injected with an average dose of 118.24 μCi of $^{124}$I-parental minibody, and whole-body PET scans were obtained beginning at 4 and ending at 21 h after administration. The microPET images at 21 h (FIG. 6) demonstrates uptake into the positive (LAPC-9) tumor and low activity in the control (PC-3) tumor as well as other vital organs. After the 21 h time-point scans, animals were sacrificed, and activity in various tissues was quantitated using a gamma-counter. The results confirm uptake in the LAPC-9 model, with an average (m=8) uptake of 4.65% ID/g (range 2.14-7.06% ID/g). Uptake by control PC-3 xenografts and activities in the liver and spleen were significantly lower than uptake in the positive tumors. At 21 hours the minibody was still in circulation, noted by blood activity averaging 3.80% ID/g.

Example 5

Further microPET Imaging of Xenografts Using 124-I anti-PSCA Diabody

Additional PSCA-specific engineered humanized antibody fragments [diabody (scFv dimer, 50 kDa), minibody (scFv-CH3 dimer, 80 kDa) and scFv-Fc, 110 kDa)] were generated, differing in their in vivo pharmacokinetics and targeting potential. Recombinant fragments were radioiodinated with the positron emitter 124I ($t_{1/2}$=4.2 d) and evaluated by microPET scanning in order to determine the optimal format for in vivo imaging. As shown in FIG. 12, the intermediate-sized minibody demonstrated excellent tumor uptake of 5.2 (±1.6) percent injected dose per gram (% ID/g) in PSCA-expressing LAPC-9 xenografts (n=12) at 21 h post-injection; rapid clearance from blood and normal tissues resulted in high contrast microPET images. The positive tumor to control tumor (PC-3) uptake ratio was 2.0, and the tumor-to-carcass ratio was 4.3.

As shown in FIG. 11, the smaller fragment (anti-PSCA diabody) cleared quickly from the circulation and only reached 0.9 (±0.3) % ID/g in LAPC-9 xenografts at 21 h (n=4). A larger scFv-Fc fragment, engineered for rapid clearance, attained 3.1 (±0.4) % ID/g in LAPC-9 xenografts compared to PC-3 (1.7±0.2% ID/g) (n=4) (FIG. 13).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An antibody that binds to Prostate Stem Cell Antigen (PSCA) comprising:
    a light chain CDR1 of a CDR1 in SEQ ID NO: 6;
    a light chain CDR2 of a CDR2 in SEQ ID NO: 6;
    a light chain CDR3 of a CDR3 in SEQ ID NO: 6;
    a heavy chain CDR1 of a CDR1 in SEQ ID NO: 7;
    a heavy chain CDR2 of a CDR2 in SEQ ID NO: 7; and
    a heavy chain CDR3 of a CDR3 in SEQ ID NO: 7.

2. The antibody of claim 1 comprising a variable light chain region of SEQ ID NO:6 and a variable heavy chain region of SEQ ID NO:7.

3. The antibody of claim 1 selected from the group consisting of scFv, scFv dimer (diabody), SC-FV-$C_H3$ dimer (minibody) and scFv-Fc.

4. The antibody of claim 3, wherein said scFv dimer comprises two scFv monomers joined by a linker.

5. The antibody of claim 4, wherein said linker comprises a peptide sequence.

6. The antibody of claim 5, wherein said peptide sequence comprises the sequence [(GGGS)2] (SEQ ID NO: 3).

7. The antibody of claim 1, wherein said antibody is a humanized antibody fragment, which binds to PCSA and has an affinity of $K_D$=2.0 nM or less.

8. The antibody of claim 1, wherein said antibody is a humanized antibody fragment, which binds to PCSA and has an affinity of $K_D$=5.5 nM or less.

9. The antibody of claim 1, wherein said antibody is a scFv dimer (diabody).

10. The antibody of claim 1, wherein said antibody is a SC-FV-$C_H3$ dimer (minibody).

* * * * *

SEQUENCE LISTING

```
<160> NUMBER OF SEQ ID NOS: 7

<210> SEQ ID NO 1
<211> LENGTH: 1182
<212> TYPE: DNA
<213> ORGANISM: Artificial Sequence
<220> FEATURE:
<223> OTHER INFORMATION: humanized anti-prostate stem cell antigen
      (PSCA) minibody
<220> FEATURE:
<221> NAME/KEY: CDS
<222> LOCATION: (1)..(1179)

<400> SEQUENCE: 1 tct aga gcc gcc acc atg gag aca gac aca ctc ctg cta tgg gtg ctg      48
Ser Arg Ala Ala Thr Met Glu Thr Asp Thr Leu Leu Leu Trp Val Leu
1               5                   10                  15 ctg ctc tgg gtt cca ggt tcc acc ggt gac att cag ctg acc caa tct      96
Leu Leu Trp Val Pro Gly Ser Thr Gly Asp Ile Gln Leu Thr Gln Ser
            20                  25                  30
```

-continued

| | | |
|---|---|---|
| cca agc tct ttg tcc gcc tct gtg ggg gat agg gtc acc atc acc tgc<br>Pro Ser Ser Leu Ser Ala Ser Val Gly Asp Arg Val Thr Ile Thr Cys<br>35 40 45 | 144 | |
| agt gcc agt tca agt gta aga ttc att cac tgg tac cag cag aaa cca<br>Ser Ala Ser Ser Ser Val Arg Phe Ile His Trp Tyr Gln Gln Lys Pro<br>50 55 60 | 192 | |
| gga aaa gct ccc aaa aga ctc atc tat gac aca tcc aaa ctg gct tct<br>Gly Lys Ala Pro Lys Arg Leu Ile Tyr Asp Thr Ser Lys Leu Ala Ser<br>65 70 75 80 | 240 | |
| ggc gtc cct tct agg ttc agt ggc tcc ggg tct ggg aca gac ttc acc<br>Gly Val Pro Ser Arg Phe Ser Gly Ser Gly Ser Gly Thr Asp Phe Thr<br>85 90 95 | 288 | |
| ctc acc att agc agt ctg cag ccg gaa gat ttc gcc acc tat tac tgt<br>Leu Thr Ile Ser Ser Leu Gln Pro Glu Asp Phe Ala Thr Tyr Tyr Cys<br>100 105 110 | 336 | |
| cag cag tgg agt agt agc cca ttc acg ttc gga cag ggg acc aag gtg<br>Gln Gln Trp Ser Ser Ser Pro Phe Thr Phe Gly Gln Gly Thr Lys Val<br>115 120 125 | 384 | |
| gag ata aaa ggc agt act agc ggc ggt ggc tcc gga ggc ggc tcc gga<br>Glu Ile Lys Gly Ser Thr Ser Gly Gly Gly Ser Gly Gly Gly Ser Gly<br>130 135 140 | 432 | |
| ggt ggc ggc agc tca gag gtt cag ctg gtg gag tct ggg ggt ggc ctt<br>Gly Gly Gly Ser Ser Glu Val Gln Leu Val Glu Ser Gly Gly Gly Leu<br>145 150 155 160 | 480 | |
| gtg cag cca ggg ggc tca ctc cgt ttg tcc tgc gca gct tct ggc ttc<br>Val Gln Pro Gly Gly Ser Leu Arg Leu Ser Cys Ala Ala Ser Gly Phe<br>165 170 175 | 528 | |
| aac att aaa gac tac tat ata cac tgg gtg cgt cag gcc cct ggt aag<br>Asn Ile Lys Asp Tyr Tyr Ile His Trp Val Arg Gln Ala Pro Gly Lys<br>180 185 190 | 576 | |
| ggc ctg gaa tgg gtt gca tgg att gat cct gag aat ggt gac act gaa<br>Gly Leu Glu Trp Val Ala Trp Ile Asp Pro Glu Asn Gly Asp Thr Glu<br>195 200 205 | 624 | |
| ttt gtc ccg aag ttc cag ggc cgt gcc act ata agc gca gac aca tcc<br>Phe Val Pro Lys Phe Gln Gly Arg Ala Thr Ile Ser Ala Asp Thr Ser<br>210 215 220 | 672 | |
| aaa aac aca gcc tac ctg cag atg aac agc ctg cgt gct gag gac act<br>Lys Asn Thr Ala Tyr Leu Gln Met Asn Ser Leu Arg Ala Glu Asp Thr<br>225 230 235 240 | 720 | |
| gcc gtc tat tat tgt aaa acg ggg ggg ttc tgg ggt caa gga acc ctg<br>Ala Val Tyr Tyr Cys Lys Thr Gly Gly Phe Trp Gly Gln Gly Thr Leu<br>245 250 255 | 768 | |
| gtc acc gtc tcg agc gag ccc aaa tct tgt gac aaa act cac aca tgc<br>Val Thr Val Ser Ser Glu Pro Lys Ser Cys Asp Lys Thr His Thr Cys<br>260 265 270 | 816 | |
| cca ccg tgc ggc gga ggt agc tct ggc ggt gga tcc ggc ggg cag ccc<br>Pro Pro Cys Gly Gly Gly Ser Ser Gly Gly Gly Ser Gly Gly Gln Pro<br>275 280 285 | 864 | |
| cga gaa cca cag gtg tac acc ctg ccc cca tcc cgg gat gag ctg acc<br>Arg Glu Pro Gln Val Tyr Thr Leu Pro Pro Ser Arg Asp Glu Leu Thr<br>290 295 300 | 912 | |
| aag aac cag gtc agc ctg acc tgc ctg gtc aaa ggc ttc tat ccc agc<br>Lys Asn Gln Val Ser Leu Thr Cys Leu Val Lys Gly Phe Tyr Pro Ser<br>305 310 315 320 | 960 | |
| gac atc gcc gtg gag tgg gag agc aat ggg cag ccg gag aac aac tac<br>Asp Ile Ala Val Glu Trp Glu Ser Asn Gly Gln Pro Glu Asn Asn Tyr<br>325 330 335 | 1008 | |
| aag acc acg cct ccc gtg ctg gac tcc gac ggc tcc ttc ttc ctc tac<br>Lys Thr Thr Pro Pro Val Leu Asp Ser Asp Gly Ser Phe Phe Leu Tyr<br>340 345 350 | 1056 | |

```
agc aag ctc acc gtg gac aag agc agg tgg cag cag ggg aac gtc ttc      1104
Ser Lys Leu Thr Val Asp Lys Ser Arg Trp Gln Gln Gly Asn Val Phe
        355                 360                 365 tca tgc tcc gtg atg cat gag gct ctg cac aac cac tac acg cag aag      1152
Ser Cys Ser Val Met His Glu Ala Leu His Asn His Tyr Thr Gln Lys
370                 375                 380 agc ctc tcc ctg tct ccg ggt aaa tga tag                              1182
Ser Leu Ser Leu Ser Pro Gly Lys
385                 390

<210> SEQ ID NO 2
<211> LENGTH: 392
<212> TYPE: PRT
<213> ORGANISM: Artificial Sequence
<220> FEATURE:
<223> OTHER INFORMATION: Synthetic Construct

<400> SEQUENCE: 2

Ser Arg Ala Ala Thr Met Glu Thr Asp Thr Leu Leu Leu Trp Val Leu
1               5                   10                  15

Leu Leu Trp Val Pro Gly Ser Thr Gly Asp Ile Gln Leu Thr Gln Ser
            20                  25                  30

Pro Ser Ser Leu Ser Ala Ser Val Gly Asp Arg Val Thr Ile Thr Cys
        35                  40                  45

Ser Ala Ser Ser Ser Val Arg Phe Ile His Trp Tyr Gln Gln Lys Pro
    50                  55                  60

Gly Lys Ala Pro Lys Arg Leu Ile Tyr Asp Thr Ser Lys Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln Trp Ser Ser Ser Pro Phe Thr Phe Gly Gln Gly Thr Lys Val
        115                 120                 125

Glu Ile Lys Gly Ser Thr Ser Gly Gly Gly Ser Gly Gly Gly Ser Gly
    130                 135                 140

Gly Gly Gly Ser Ser Glu Val Gln Leu Val Glu Ser Gly Gly Gly Leu
145                 150                 155                 160

Val Gln Pro Gly Gly Ser Leu Arg Leu Ser Cys Ala Ala Ser Gly Phe
                165                 170                 175

Asn Ile Lys Asp Tyr Tyr Ile His Trp Val Arg Gln Ala Pro Gly Lys
            180                 185                 190

Gly Leu Glu Trp Val Ala Trp Ile Asp Pro Glu Asn Gly Asp Thr Glu
        195                 200                 205

Phe Val Pro Lys Phe Gln Gly Arg Ala Thr Ile Ser Ala Asp Thr Ser
    210                 215                 220

Lys Asn Thr Ala Tyr Leu Gln Met Asn Ser Leu Arg Ala Glu Asp Thr
225                 230                 235                 240

Ala Val Tyr Tyr Cys Lys Thr Gly Gly Phe Trp Gly Gln Gly Thr Leu
                245                 250                 255

Val Thr Val Ser Ser Glu Pro Lys Ser Cys Asp Lys Thr His Thr Cys
            260                 265                 270

Pro Pro Cys Gly Gly Gly Ser Ser Gly Gly Gly Ser Gly Gly Gln Pro
        275                 280                 285

Arg Glu Pro Gln Val Tyr Thr Leu Pro Pro Ser Arg Asp Glu Leu Thr
    290                 295                 300
```

```
Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Val Leu Asp Ser Asp Gly Ser Phe Phe Leu Tyr
            340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
    370                 375                 380

Ser Leu Ser Leu Ser Pro Gly Lys
385                 390

<210> SEQ ID NO 3
<211> LENGTH: 8
<212> TYPE: PRT
<213> ORGANISM: Artificial Sequence
<220> FEATURE:
<223> OTHER INFORMATION: synthetic peptide linker

<400> SEQUENCE: 3

Gly Gly Gly Ser Gly Gly Gly Ser
1               5

<210> SEQ ID NO 4
<211> LENGTH: 4
<212> TYPE: PRT
<213> ORGANISM: Artificial Sequence
<220> FEATURE:
<223> OTHER INFORMATION: synthetic peptide linker

<400> SEQUENCE: 4

Gly Gly Gly Ser
1

<210> SEQ ID NO 5
<211> LENGTH: 5
<212> TYPE: PRT
<213> ORGANISM: Artificial Sequence
<220> FEATURE:
<223> OTHER INFORMATION: synthetic peptide linker

<400> SEQUENCE: 5

Gly Gly Gly Gly Ser
1               5

<210> SEQ ID NO 6
<211> LENGTH: 106
<212> TYPE: PRT
<213> ORGANISM: Artificial Sequence
<220> FEATURE:
<223> OTHER INFORMATION: synthetic peptide linker

<400> SEQUENCE: 6

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60
```

```
Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys
            100                 105

<210> SEQ ID NO 7
<211> LENGTH: 112
<212> TYPE: PRT
<213> ORGANISM: Artificial Sequence
<220> FEATURE:
<223> OTHER INFORMATION: synthetic peptide linker

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Ile His Trp Val Arg Gln Ala Pro Gly Lys Gly Leu Glu Trp Val
                35                  40                  45

Ala Trp Ile Asp Pro Glu Asn Gly Asp Thr Glu Phe Val Pro Lys Phe
        50                  55                  60

Gln Gly Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Lys Thr Gly Gly Phe Trp Gly Gln Gly Thr Leu Val Thr Val Ser Ser
            100                 105                 110
```